(12) United States Patent
Karlsson et al.

(10) Patent No.: US 9,187,509 B2
(45) Date of Patent: Nov. 17, 2015

(54) CALMANGAFODIPIR, A NEW CHEMICAL ENTITY, AND OTHER MIXED METAL COMPLEXES, METHODS OF PREPARATION, COMPOSITIONS, AND METHODS OF TREATMENT

(71) Applicant: PledPharma AB, Stockholm (SE)

(72) Inventors: Jan-Olof Karlsson, Trondheim (NO); Karl Reineke, Niskayuna, NY (US); Tino Kurz, Linköping (SE); Rolf Andersson, Vikingstad (SE); Michael Hall, Albany, NY (US); Christina McLaughlin, Albany, NY (US); Sven Jacobsson, Stockholm (SE); Jacques Näsström, Bromma (SE)

(73) Assignee: Pled Pharma AB, Stockholm (SE)

( * ) Notice: Subject to any disclaimer, the term of this patent is extended or adjusted under 35 U.S.C. 154(b) by 0 days.

(21) Appl. No.: 14/369,153

(22) PCT Filed: Dec. 4, 2012

(86) PCT No.: PCT/IB2012/056959
§ 371 (c)(1),
(2) Date: Jun. 26, 2014

(87) PCT Pub. No.: WO2013/102806
PCT Pub. Date: Jul. 11, 2013

(65) Prior Publication Data
US 2015/0005259 A1    Jan. 1, 2015

Related U.S. Application Data

(60) Provisional application No. 61/583,377, filed on Jan. 5, 2012, provisional application No. 61/656,178, filed on Jun. 6, 2012, provisional application No. 61/668,679, filed on Jul. 6, 2012, provisional application No. 61/721,575, filed on Nov. 2, 2012.

(51) Int. Cl.
| C07F 19/00 | (2006.01) |
|---|---|
| A61K 31/555 | (2006.01) |
| C07F 13/00 | (2006.01) |

(52) U.S. Cl.
CPC .............. *C07F 13/005* (2013.01); *C07F 19/00* (2013.01)

(58) Field of Classification Search
USPC ...................... 546/6, 2; 514/188, 89
See application file for complete search history.

(56) References Cited

U.S. PATENT DOCUMENTS

| 4,933,456 | A | * | 6/1990 | Rocklage et al. ............... 546/5 |
|---|---|---|---|---|
| 5,091,169 | A | | 2/1992 | Rocklage et al. |
| 5,223,243 | A | | 6/1993 | Rocklage et al. |
| 6,147,094 | A | | 11/2000 | Towart et al. |
| 6,258,828 | B1 | | 7/2001 | Towart et al. |
| 6,310,051 | B1 | | 10/2001 | Karlsson et al. |
| 6,391,895 | B1 | | 5/2002 | Towart et al. |
| 7,351,722 | B2 | | 4/2008 | Batteux et al. |
| 2004/0142907 | A1 | | 7/2004 | Batteux et al. |
| 2007/0148154 | A1 | | 6/2007 | Weill et al. |
| 2009/0155184 | A1 | | 6/2009 | Erikson et al. |

FOREIGN PATENT DOCUMENTS

| EP | 0290047 A2 | 11/1988 |
|---|---|---|
| EP | 0936915 B1 | 10/2002 |
| EP | 0910360 B1 | 11/2002 |
| EP | 1060174 B1 | 9/2004 |
| EP | 1054670 B1 | 3/2005 |
| EP | 1381364 B1 | 8/2006 |
| WO | 97/49409 A1 | 12/1997 |
| WO | 02/087579 A1 | 11/2002 |

(Continued)

OTHER PUBLICATIONS

Rocklage et al, Inorganic Chemistry, 28:477-485 (1989).
Elst et al, Investigative Radiology, 32(10):581-588 (1997).
Alexandre et al, Journal of the National Cancer Institute, vol. 98, No. 4, pp. 236-244, Feb. 15, 2006.
Bedda et al, Journal of Hepatology, 39 (2003) pp. 765-772.
Burok et al, Biochemical and Biophysical Research Communications, 254:768-772 (1999).
Crossgrove et al, NMR in Biomedicine (2004);17:544-553.

(Continued)

*Primary Examiner* — Charanjit Aulakh
(74) *Attorney, Agent, or Firm* — Porter Wright Morris & Arthur LLP

(57) ABSTRACT

A mixed metal complex of a compound of Formula I, or a salt thereof, wherein the mixed metals comprise a Group III-XII transition metal and a Group II metal:

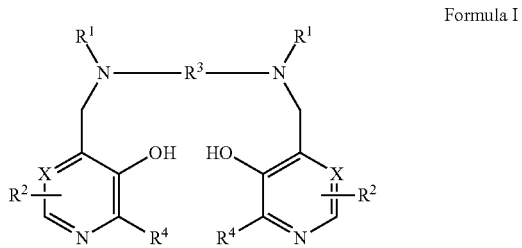

Formula I wherein X, $R^1$, $R^2$, $R^3$, and $R^4$ are as defined herein, is produced in a one step crystallization from a solution of the Group III-XII transition metal, the Group II metal, and a compound of Formula I. Methods for treatment of a pathological condition in a patient, for example, a pathological condition caused by the presence of oxygen-derived free radicals, comprise administering the mixed metal complex to the patient.

41 Claims, 21 Drawing Sheets

(56) References Cited

FOREIGN PATENT DOCUMENTS

| WO | 2009/078794 A1 | 6/2009 |
|---|---|---|
| WO | 2011/004325 A1 | 1/2011 |

OTHER PUBLICATIONS

Cizewski Culotta et al, NIH Public Access Author Manuscript, published as Biochim Biophys Acta. (2006) 1763 (7): 747-758.
Cuzzocrea et al, Pharmacol Rev 53:135-159, 2001.
Doroshow, Journal of the National Cancer Institute, vol. 98, No. 4, pp. 223-225, Feb. 15, 2006.
Folin et al, BioMetals 1994, 7:75-79.
Fridovich, The Journal of Experimental Biology, 201:1203-1209 (1998).
Hazell et al, Neuroscience Letters, 396 (2006) 167-171.
Hustvedt et al, Acta Radiologica, 38 (1997) 690-699.
Karlsson, Letters to the Editor / Journal of Hepatology, 40 (2004) 872-873.
Karlsson et al, Acta Radiologica, 42 (2001) 540-547.
Karlsson et al, Letters to the Editor / Cancer Res 2006; 66: (1). Jan. 1, 2006, p. 598.
King et al, Zinc Homeostasis in Humans1, The Journal of Nutrition (2000), pp. 1360s-1366s.
Laurent et al, Cancer Research, 2005; 65(3):948-956, Feb. 1, 2005.
Muscoli et al, British Journal of Pharmacology (2003) 140, 445-460.
Scheuhammer et al, Arch. Environm. Contam. Toxicol., 11:515-520 (1982).
Schmidt et al, J Biol Inorg Chem (2002) 7: 241-248.
Skjold et al, Journal of Magnetic Resonance Imaging, 20:948-952 (2004).
Southon et al, Acta Radiologica, 38 (1997) 708-716.
Toft et al, Acta Radiologica 38 (1997) 677-689.
Wendland, NMR in Biomedicine, 2004;17:581-594.
Yokel, Environmental Health Perspectives, vol. 110, Supplement 5, Oct. 2002, 699-704.
Yri et al, Acta Oncologica, Jan. 2009, 1-3 (online).
Kurz et al, Translation Oncology, 5(4):252-259 (Aug. 2012).
Agarwal et al., Acetaminophen-Induced Hepatotoxicity in Mice Occurs with Inhibition of Activity and Nitration of Mitochondrial Manganese Superoxide Dismutase, The Journal of Pharmacology and Experimental Therapeutics, 337:110-116 (2011).
Beckman et al., Nitric oxide, superoxide, and peroxynitrite: the good, the bad, and ugly, American Journal of Physiology—Cell Physiology, 271:C1424-C1437 (1996).
Burkhead et al., Systems biology approach to Wilson's disease, Biometals, 24(3):455-466 (Jun. 2011).
Citrin et al., Radioprotectors and Mitigators of Radiation-Induced Normal Tissue Injury, The Oncologist, 15:360-371 (2010).
Coriat et al., Mangafodipir Protects against Hepatic Ischemia—Reperfusion Injury in Mice, PLoS One, 6:1-8 (Nov. 2011).
Elizondo et al., Preclinical Evaluation of MnDPDP: New Paramagnetic Hepatobiliary Contrast Agent for MR Imaging, Radiology, 178:73-78 (Jan. 1991).
Farrell et al., Hepatic Microcirculation in Fatty Liver Disease, The Anatomical Record, 291:684-692 (2008).
Forstermann et al., Therapeutic effect of enhancing endothelial nitric oxide synthase (eNOS) expression and preventing eNOS uncoupling, British Journal of Pharmacology, 164:213-223 (2011).
Garcia-Monzon et al., Intrahepatic accumulation of nitrotyrosine in chronic viral hepatitis is associated with histological severity of liver disease, Journal of Hepatology, 32:331-338 (2000).
Karlsson et al., First Clinical Experience with the Magnetic Resonance Imaging Contrast Agent and Superoxide Dismutase Mimetic Mangafodipir as an Adjunct in Cancer Chemotherapy—A Translational Study, Translational Oncology, 5(1):32-38 (Feb. 2012).
Joseph A. Knight M.D., Reactive Oxygen Species and the Neurodegenerative Disorders, Annals of Clinical and Laboratory Science, 27(1):11-25 (1997).
Koruk et al. Oxidative Stress and Enzymatic Antioxidant Status in Patients with Nonalcoholic Steatohpatitis, Annals of Clinical & Laboratory Science, 34(1):57-62 (2004).
MacMillan-Crow et al., Nitration and inactivation of manganese superoxide dismutase in chronic rejection of human renal allografts, Proc. Natl. Acad. Sci., 93:11853-11858 (Oct. 1996).
Rachmilewitz et al., Role of Iron in Inducing Oxidative Stress in Thalassemia, Can It Be Prevented by Inhibition of Absorption and by Antioxidants?, New York Academy of Sciences, 1054:118-123 (2005).
Rafael Radi, Nitric oxide, oxidants, and protein tyrosine nitration, PNAS, 101(12):4003-4008, Mar. 23, 2004.
Towart, Manganese dipyridoxyl diphosphate protects against acute anthracycline-induced cardiotoxicity in mice, Pharmacology of the Heart, Abstract 36.52, p. 26, 1998.
Wong et al., Post exposure administration of A1 adenosine receptor agonists attenuates noise-induced hearing loss, Hearing Research, 260:81-88 (2010).

\* cited by examiner

M = 0.8 Ca : 0.2 Mn $C_{22}H_{27}MN_4Na_3O_{14}P_2$
fwt: 745.43

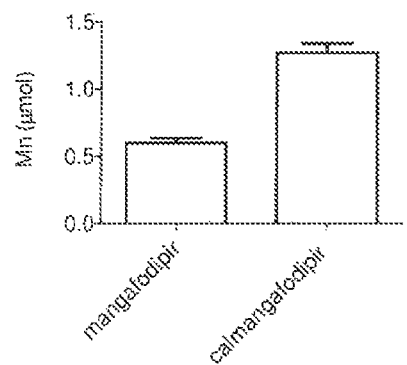
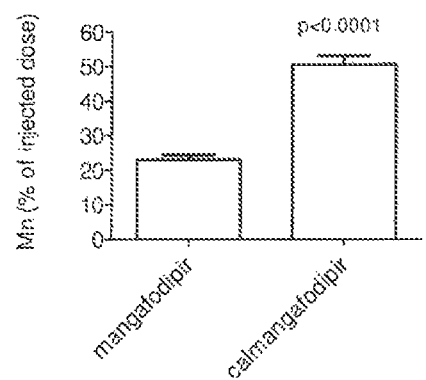
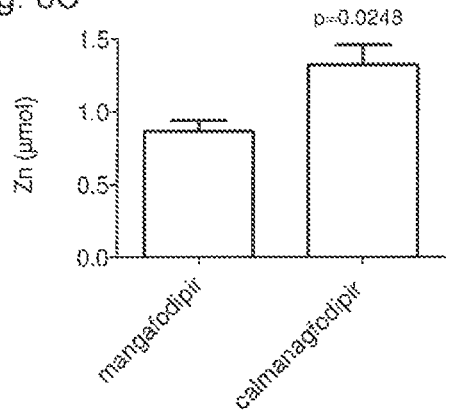

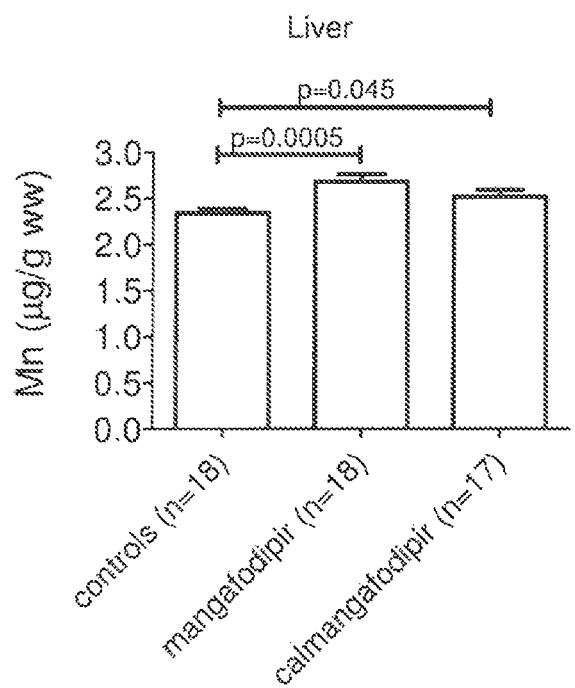

CALMANGAFODIPIR, A NEW CHEMICAL ENTITY, AND OTHER MIXED METAL COMPLEXES, METHODS OF PREPARATION, COMPOSITIONS, AND METHODS OF TREATMENT

FIELD OF THE INVENTION

The present invention is directed to a mixed metal complex of a dipyridoxyl compound, for example, N,N'-bis-(pyridoxal-5-phosphate)-ethylenediamine-N,N'-diacetic acid (DPDP or fodipir) or other compounds of Formula I (hereafter PyridoxyL EthylDiamine derivatives or PLED-derivatives), wherein the mixed metals comprise a Group III-XII transition metal and a Group II metal. In specific embodiments, the mixed metal complex is a calcium and manganese complex. The present invention is also directed to compositions containing such a mixed metal complex, methods for preparing such a mixed metal complex, for example, in a single step crystallization, and treatment methods employing such a mixed metal complex. Such treatment methods include methods conventionally employing manganese-DPDP complexes for therapeutic effect. In a specific embodiment, the compositions may be used in the treatment of pathological conditions caused by the presence of oxygen-derived free radicals in the body, i.e., oxidative stress. The mixed metal complexes, and particularly the mixed calcium-manganese complex calmangafodipir described herein, constitute new chemical entities.

BACKGROUND OF THE INVENTION

Oxidative stress begins with the generation of reactive oxygen species (ROS) and reactive nitrogen species (RNS) as a part of normal cellular function. There are multiple cellular sources of ROS generation but the most significant ones are the mitochondria electron transport complexes I and III, P450 enzymes within the endoplasmic reticulum, and membrane bound NADPH oxidase. ROS production by each of these sources can be stimulated by cytokines, inflammation, viral proteins, and other mechanisms, like chemotherapy drugs, ischemia-reperfusion, and iron and copper overload. Importantly, these processes initially generate the free-radical superoxide ($.O_2^-$) which is sequentially reduced to form hydrogen peroxide, hydroxyl radical and, ultimately, water. Under conditions of high oxidative stress and consequently high production of superoxide, these reactive intermediates, however, readily interact with other molecules to form secondary harmful ROS, such as lipid peroxidation products and peroxynitrite (Singal et al., Liver Int. 2011; 31:1432-1448). This indicates the importance of keeping the cellular amount of superoxide under tight control. Under normal conditions this is achieved by superoxide dismutases (SODs). Although SODs have the fastest reaction rate of known enzymes, under conditions of high oxidative stress, these enzymes may be outcompeted and even irreversible irreversibly inactivated by ROS and RNS. This in turn, opens up for therapeutic use of low molecular drugs that mimic the SOD enzymes, i.e., the so-called SOD mimetics, to combat pathological oxidative stress.

Short-lived but highly reactive oxygen-derived free radicals have long been known to participate in pathological tissue damage, especially during treatment with cytotoxics/cytostatics and radiotherapy in cancer patients (Towart et al., Arch Pharmacol 1998; 358 (Suppl 2):R626, Laurent et al., Cancer Res 2005; 65:948-956, Karlsson et al., Cancer Res 2006; 66:598, Alexandre et al., J Natl Cancer Inst 2006; 98:236-244, Doroshow, J Natl Cancer Inst 2006; 98:223-225, Citrin et al, Oncologist, 2010; 15:360-371, Kurz et al., Transl Oncol 2012; 5:252-259), acetaminophen-induced liver failure (Bedda et al., J Hepatol 2003; 39:765-772; Karlsson, J Hepatol 2004; 40:872-873), in ischemic heart disease (Cuzzocrea et al., Pharmacol Rev 2001; 53:135-159) and in various neurodegenerative diseases, including Alzheimer's disease, amyotrophic lateral sclerosis (ALS), Parkinson's disease, and multiple sclerosis (Knight, Ann Clin Lab Sci. 1997; 27:11-25). Overproduction of oxygen-derived free radicals is also implicated in pathological conditions of iron overload (Rachmilewitz et al., Ann N Y Acad Sci. 2005; 1054:118-23), for example, in thalassemia, sickle cell anemia and transfusional hemosiderosis. Oxygen-derived free radicals are also implicated in hepatitis-induced liver cirrhosis (Farrell et al., Anat Rec 2008; 291:684-692) and in noise-induced hearing loss (Wong et al., Hear Res 2010; 260:81-88).

The use of dipyridoxyl based chelating agents and their metal chelates and certain manganese-containing compounds, in particular manganese chelates, in medicine is known. See EP 0910360, U.S. Pat. No. 6,147,094, EP 0936915, U.S. Pat. No. 6,258,828, EP 1054670, U.S. Pat. No. 6,310,051, EP 1060174, and U.S. Pat. No. 6,391,895, for example, which disclose that certain chelating agents, in particular dipyridoxyl chelating agents, and their metal chelates, are effective in treating or preventing anthracycline-induced cardiotoxicity, radiation-induced toxicity, ischemia-reperfusion-induced injuries, and paracetamol (acetaminophen) induced liver failure, or from a more general point of view, every pathological condition caused by the presence of oxygen-derived free radicals, i.e., oxidative stress, in humans and animals. Furthermore, the dipyridoxyl compound mangafodipir (MnDPDP) has in addition and surprisingly been found to possess cytotoxic effects against cancer cells (EP 16944338). However, as described in WO 2009/078794 A1 and in Kurz et al., 2012, this is an inherent property of fodipir (DPDP) alone or its dephosphorylated counterparts, DPMP and PLED, and not of the metal complex MnDPDP or its dephosphorylated counterparts, MnDPMP and MnPLED.

One of the MnPLED-derivatives, namely manganese N,N'-bis-(pyridoxal-5-phosphate)-ethylenediamine-N,N'-diacetic acid (Manganese DiPyridoxyl DiPhosphate; MnDPDP), also known as mangafodipir, is approved for use as a diagnostic MRI contrast agent in humans. Interestingly, mangafodipir has also been shown to protect mice against serious side effects of several cytotoxic/cytostatic drugs (doxorubicin, oxaliplatin, 5-fluorouracil and paclitaxel), without interfering negatively with the anticancer effects of these drugs (Towart et al., 1998, Laurent et al., 2005, Karlsson et al., 2006, Alexandre et al., 2006, Doroshow, 2006, Kurz et al., 2012). Mangafodipir has been tested in one colon cancer patient going through palliative treatment with a combination of folinate, 5-fluorouracil and oxaliplatin (Yri et al., Acta Oncol. 2009; 48:633-635). The preclinical data and the results from this single patient were so promising that clinical testing in cancer patients has started. When it comes to the most troublesome side effect of oxaliplatin, namely oxaliplatin-induced sensory neurotoxicity, no preclinical data exist, to the best of our knowledge, showing protective effects of mangafodipir (Karlsson et al., Transl Oncol. 2012; 5:32-38). Yri et al., 2009, described that the patient received 15 full-doses of "Nordic FLOX". In 14 of the cycles, the patient received pretreatment with mangafodipir. The patient received an accumulated dose of 1275 mg/m$^2$ oxaliplatin, which is a dose likely to give neurotoxic symptoms. No neurotoxic symptoms were detected, except during the fifth cycle when mangafodipir was deliberately left out and the patient experienced peripheral sensory neuropathy. This suggests that mangafodipir may protect against peripheral neurotoxicity. After five cycles, the performance status for the patient was drastically improved, and the demand for analgesics was significantly reduced. Neutropenia did not occur during any of the chemotherapy cycles.

A first feasibility study (MANFOL I) has been completed and positive results, including myeloprotective effects, have been reported to the Swedish Medical Agency and have been published (Karlsson et al., 2012).

Mangafodipir has also been described to protect mice against acetaminophen-induced acute liver failure in mice (ALF) (Bedda et al., 2003; Karlsson, 2004). ALF is characterized by massive hepatocyte cell death, a condition caused by glutathione depletion, oxygen-derived free radicals and mitochondrial damage.

Mangafodipir is a pro-drug in the sense that it probably has to be metabolized into N,N'-dipyridoxyl ethylenediamine-N,N'-diacetic acid (MnPLED) before it can exert cytoprotective effects during in vivo conditions (e.g., see Karlsson et al., Acta Radiol 2001; 42:540-547; Kurz et al., 2012). Manganese is an essential as well as potentially neurotoxic metal. It has been known for many years that under conditions of chronic exposure to high levels of manganese, a syndrome of extrapyramidal dysfunction similar to Parkinson's syndrome, although clinically a different disease entity, frequently occurs (see Scheuhammer & Cherian, Arch Environm Contam Toxicol 1982; 11:515-520). When a diagnostic MR imaging dose of mangafodipir is intravenously injected into humans, about 80% of the administered manganese is released (Toft et al., Acta Radiol 1997; 38:677-689). Release of paramagnetic manganese is in fact a prerequisite for the diagnostic MR imaging properties of mangafodipir (Wendland, N M R Biomed 2004; 17:581-594). Elizondo et al., 1991 (Radiology 1991; 178:73-78) stated that the fodipir moiety binds to the pyridoxyl 5' phosphate receptor on hepatocytes and ensures a high intracellular concentration of mangafodipir in the liver. This hypothesis was recently also suggested in a paper by Coriat et al., (PLoS One 2011; 6:1-6, e27005). This is a nice hypothesis but unfortunately an unproven and a very unlikely one, which fell out of fashion shortly after it had been presented. When mangafodipir is injected intravenously (i.v.) about 80% of the metal complex falls apart (Toft et al., Radiol 1997), and at every equimolar Mn dose, $MnCl_2$ has an equal or better liver MR imaging contrast efficacy than mangafodipir (Southon et al., Acta Radiol 1997). Furthermore, after injection of mangafodipir almost all fodipir is recovered in the urine (the major part of it as PLED), whereas most manganese is recovered in the feces (Hustvedt et al., Acta Radiol 1997; 38:690-699). On the other hand, the therapeutic effects of mangafodipir (MnDPDP) and its dephosphorylated counterparts MnDPMP (N,N'-dipyridoxylethylenediamine-N,N'-diacetate-5-phosphate) and MnPLED depend on the intact metal complex (Brurok et al., Biochem Biophys Res Commun. 1999; 254:768-721, Karlsson et al 2001; 42:540-547).

PLED-derivatives mimic the mitochondrial enzyme manganese superoxide dismutase (MnSOD) (Brurok et al., 1999). MnSOD protects the mammalian cell from the superoxide radical, a byproduct from oxygen metabolism, which is produced in fairly high amounts during normal aerobic conditions; no mammalians survive without a functional MnSOD. MnSOD has the fastest turnover number (reaction rate with its substrate) of any known enzyme ($>10^9 M^{-1} s^{-1}$) (Fridovich, J Exp Biol. 1998; 201:1203-1209). Low molecular weight MnSOD mimetics may have turnover rates close to that of native MnSOD (Cuzzocrea et al., 2001). Interestingly, physiological buffers containing transition metals like manganese may have similar high turnover numbers (Culotta et al., Biochim Biophys Acta. 2006; 1763:747-758). However, the importance of native SOD enzymes is consistent with a selection process favoring organisms that elaborate a means of localizing transition metal catalyst for superoxide dismutation to parts of the cell where there is a high need for such dismutation, e.g., mitochondria. Furthermore, results from myocardial ischemia-reperfusion in anaesthetized pigs inevitably show that the intact MnPLED, but not manganese per se, protects against oxidative stress, seen as reduction in infarct size (Karlsson et al., 2001). Effective inactivation of superoxide is essential in preventing generation of very devastating hydroxyl radicals and peroxynitrite (Cuzzocrea et al., 2001). During pathological oxidative stress, the formation of superoxide radicals often exceeds the endogenous capacity for inactivation. Furthermore, superoxide stimulates production of peroxynitrite which nitrates endogenous MnSOD. This protein is nitrated by peroxynitrite in Tyr-34 (Radi, Proc Natl Acad Sci USA 2004; 101:4003-4008). Once nitrated, MnSOD looses its enzymatic activity, an event favoring the accumulation of superoxide and superoxide-driven damage (Muscoli et al., Br J Pharmacol 2003; 140:445-460).

Recent results indicate that MnSOD inactivation by nitration is an early event in paracetamol-induced hepatic toxicity (Agarwal et al., J Pharmacol Exp Ther 2011; 337:110-116). Old results, in addition, indicate that nitration and inactivation of MnSOD are involved in chronic rejection of transplanted kidneys in humans (MacMillan-Crow et al., Proc Natl Acad Sci USA 1996; 93:11853-11858). It may also be relevant to note that actin, which can constitute 5% or more of the cell protein, is heavily nitrated in sickle cell anemia and that the extent of nitration observed is sufficient to induce cytoskeletal polymerization (Radi, 2004). Circulating levels of 3-nitrotyrosine may in addition serve as a biomarker to assess atherosclerosis risks. Furthermore, in addition to atherosclerosis, peroxinitrite and 3-nitrotyrosine are believed to be involved in myocardial ischemia, septic and distressed lung, inflammatory bowel disease, amyotrophic lateral sclerosis (Beckman et al., Am J Physiol 1996; 271:C1424-C1437) and diabetes (Fönstermann et al, Br J Pharmacol. 2011; 164:213-223).

Impaired antioxidant defense mechanisms, including reduced SOD activity, and a subsequently increased production of peroxynitrite, may be an important factor in the pathogenesis of non-alcoholic steatohepatitis (NASH) (Koruk et al., Ann Clin Lab Sci. 2004; 34:57-62). A major epidemiological and clinical association between either hepatitis B or hepatitis C virus infections and the development of chronic hepatitis and the appearance of hepatocellular carcinoma is evident. Interestingly, peroxynitrite-induced tyrosine-nitration is markedly increased in patients with chronic viral hepatitis (Garcia-Monzon et al., J Hepatol. 2000; 32:331-338). Currently, the generally cited mechanism of pathology development in Wilson's disease involves oxidative damage due to copper overload. Generation of reactive oxygen species (ROS) as well as lipid oxidation and DNA damage has been detected in the liver, particularly at the advanced stages of this disease (Burkhead et al., Biometals 2011; 24:455-466).

MnPLED-derivatives are not targets for peroxynitrite and addition of exogenous MnPLED-derivatives may in such situations re-establish the protective potential. PLED-derivatives are in addition strong iron binders, as described in EP 1054670, U.S. Pat. No. 6,310,051 and by Rocklage et al., (Inorg Chem 1989; 28:477-485), and some MnPLED-derivatives may have catalase and glutathione reductase activities (Laurent et al., 2005), which may further increase their antioxidant capacity.

For diagnostic imaging use and other sporadic use, dissociation of manganese from mangafodipir presents no major toxicological problem. Due to uptake into CNS, however, for more frequent use, for example in therapeutic methods, accumulated manganese toxicity may represent a serious neurotoxicological problem (Crossgrove et al, NMR Biomed. 2004; 17:544-53). Thus, for more frequent therapeutic use, compounds that readily dissociate manganese should be avoided and there is a need to develop means for obtaining desirable therapeutic effects while reducing the undesirable side effects associated with such therapeutic use.

SUMMARY OF THE INVENTION

The complexes, compositions and methods of the present invention provide improvements in the preparation and use of metal complexes of PLED derivatives. In one embodiment, the invention is directed to a mixed metal complex of a compound of Formula I, or a salt thereof, wherein the mixed metals comprise a Group III-XII transition metal and a Group II metal:

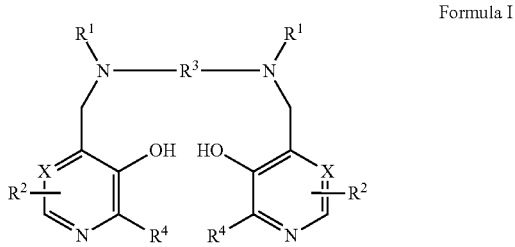

Formula I wherein
X represents CH or N,
each $R^1$ independently represents hydrogen or —$CH_2COR^5$; $R^5$ represents hydroxy, optionally hydroxylated alkoxy, amino or alkylamido;
each $R^2$ independently represents $ZYR^6$ wherein Z represents a bond or a $C_{1-3}$ alkylene or oxoalkylene group, optionally substituted by $R^7$;
Y represents a bond, an oxygen atom or $NR^6$;
$R^6$ is a hydrogen atom, $COOR^8$, alkyl, alkenyl, cycloalkyl, aryl or aralkyl group, optionally substituted by one or more groups selected from $COOR^8$, $CONR^8{}_2$, $NR^8{}_2$, $OR^8$, =$NR^8$, =O, $OP(O)(OR^8)R^7$ and $OSO_3M$;
$R^7$ is hydroxy, optionally hydroxylated, optionally alkoxylated alkyl or aminoalkyl group;
$R^8$ is a hydrogen atom or an optionally hydroxylated, optionally alkoxylated alkyl group;
M is a hydrogen atom or one equivalent of a physiologically tolerable cation;
$R^3$ represents a $C_{1-8}$ alkylene, a 1,2-cykloalkylene, or a 1,2-arylene group, optionally substituted with $R^7$; and
each $R^4$ independently represents hydrogen or $C_{1-3}$ alkyl, or a salt thereof.

In another embodiment, the invention is directed to a calcium and manganese complex of a compound of Formula I. The mixed metal complexes, and particularly the mixed calcium-manganese complex calmangafodipir described herein, constitute new chemical entities.

The present invention is also directed to methods of producing a mixed metal complex which comprises a one-step crystallization from a solution of the Group III-XII transition metal, the Group II metal, and a compound of Formula I.

In another embodiment, the invention is directed to a method of treatment of a pathological condition in a patient, comprising administering to the patient a mixed metal complex according to the invention, optionally together with one or more physiologically acceptable carriers and/or excipients.

The complexes according to the invention are advantageous in that the Group II metal stabilizes the complex from releasing the Group III-XII transition metal. This reduces toxic effects associated with use of previous Group III-XII transition metal complexes, for example, MnPLED derivatives such as mangafodipir. The complexes of the invention may also exhibit improved treatment of and/or protection against pathological conditions, particularly those caused by the presence of oxygen-derived free radicals, i.e., oxidative stress. Additional improvements and advantages of the present invention will be more apparent in view of the Detailed Description set forth below.

BRIEF DESCRIPTION OF THE DRAWINGS

The following Detailed Description will be more fully understood in view of the drawings, wherein:

FIG. 6A shows the increase in manganese (Mn) content in 0-24 h urine, expressed as the total content of Mn minus the basal content of Mn, from rats injected with mangafodipir or calmangafodipir containing 2.59 μmol and 2.52 μmol Mn, respectively. FIG. 6B shows the increase in urine content of Mn expressed as percentage of the injected dose. FIG. 6C shows the increase in zinc content 24 h urine in the same animals. Results are expressed as mean±S.E.M.; n=4 in each group. These figures are more fully described in Example 4.

FIGS. 11A-11C show the Mn content of the brain, pancreas and liver, respectively, after 39 doses of either NaCl (controls), mangafodipir or calmangafodipir (corresponding in both cases to an accumulated dose of 2800 μmol/kg manganese). Results are expressed as mean±S.E.M.; n=17-18 in each group, as described in Example 8.

Figure 1:
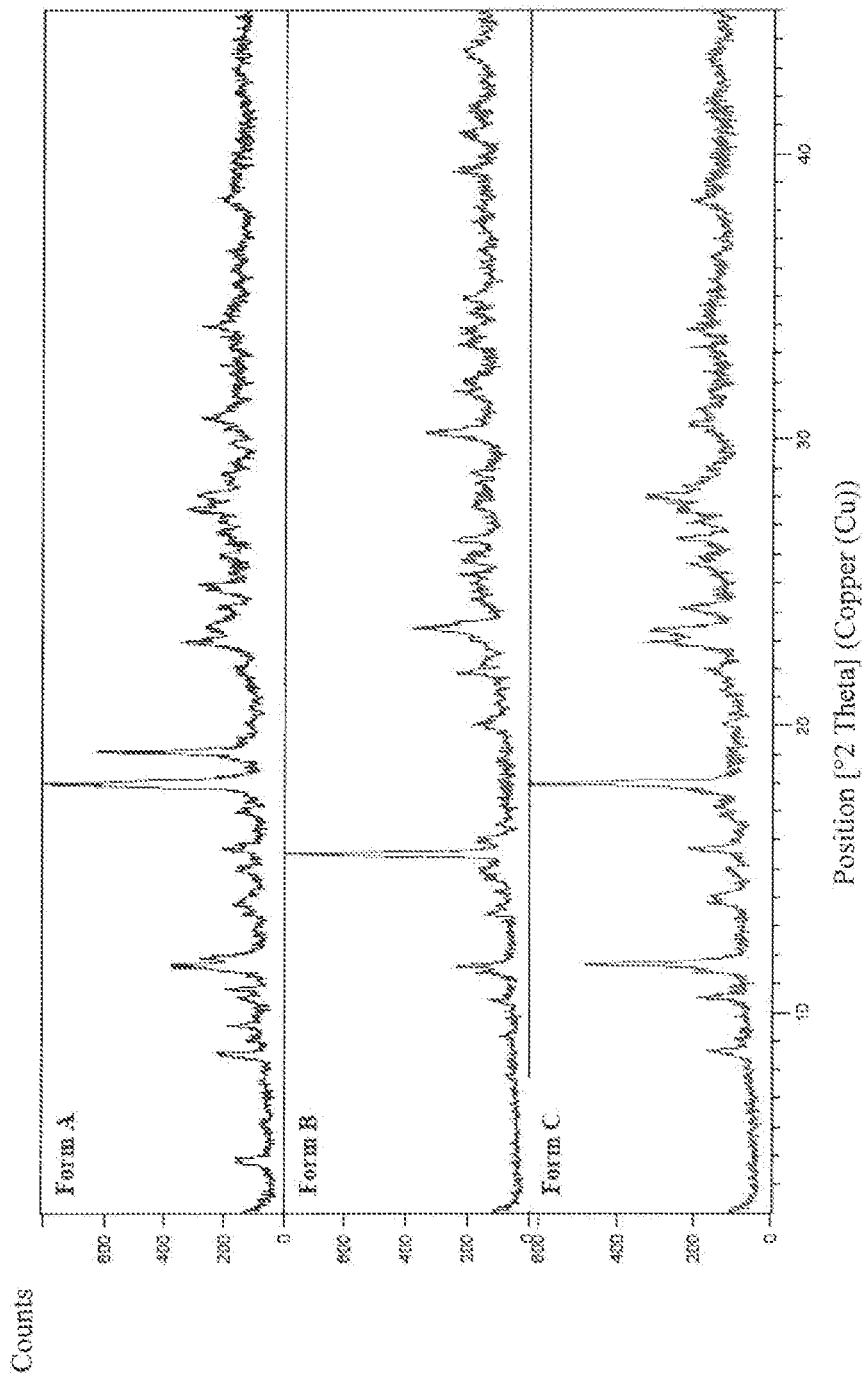
FIG. 1 shows X-ray powder diffraction (XRPD) patterns for three crystalline forms of a calcium manganese complex of fodipir (DPDP) having an approximate Ca:Mn molar ratio of about 4:1, referred to herein as "calmangafodipir", obtained in a one-step crystallization method according to the invention, as described in Example 1.

The drawings will be more fully understood in view of the Examples.

DETAILED DESCRIPTION

The complexes, compositions and methods of the present invention provide improvements in the preparation and use of metal complexes of PLED derivatives, i.e., PyridoxyL Ethyl-Diamine-derivatives, although it is recognized that the derivatives also act as pro-drugs of PLED as they can metabolize to form PLED in vivo.

WO 2011/004325 A1 demonstrates how added surplus of fodipir (DPDP) to mangafodipir (MnDPDP) stabilizes it from releasing manganese after administration and thereby reduces uptake to CNS, and thereby lowers the neurotoxic potential of mangafodipir considerably. Since it is the intact manganese-containing complex that exerts SOD-mimetic and cytoprotective effects, surplus of fodipir will therefore not only lower the neurotoxic potential but it will also increase the cytoprotective efficacy considerably.

In vivo-release of manganese from MnPLED-derivatives, including Manganese N,N'-bis-(pyridoxal-5-phosphate)-ethylenediamine-N,N'-diacetic acid (mangafodipir), depends on the presence of free or readily dissociable zinc in the body. Zinc has about 1000 times higher affinity than manganese for fodipir or its dephosphorylated counterparts (Rocklage et al., 1989). Experimental studies suggest that manganese release in vivo from mangafodipir saturates at doses exceeding 5 μmol/kg (Southon et al., 1997). Cardiac and liver imaging with mangafodipir in healthy volunteers indicates a similar saturation dose in man (Skjold et al., J. Magn. Reson. Imaging 2004; 20:948-952, Toft et al., 1997).

In the invention described in WO 2011/004325 A1, the particular therapeutic composition was assumed to be obtained by mixing two active pharmaceutical ingredients (APIs), e.g., mangafodipir and fodipir, in a ready-to-use solution or administering them separately. It was demonstrated that fodipir at a dose level around 5 to 10 μmol/kg had a considerable in vivo stabilizing effect on mangafodipir. The first clinical experiences (Yri et al., 2009 and Karlsson et al., 2011) show that mangafodipir is therapeutically efficacious at a dose level somewhere between 2 and 10 μmol/kg in man. Taking in consideration the higher efficacy of mangafodipir plus fodipir, it is reasonable to presume that mangafodipir should be therapeutically efficacious in patients at a dose level close to 1 μmol/kg. This, in turn, teaches us that a (fodipir+mangafodipir)/mangafodipir ratio close to 5, i.e., a ready-to-use formulation containing 4 times more fodipir than mangafodipir, should be efficacious. This furthermore suggests a ready-to-use formulation containing 40 mM fodipir and 10 mM mangafodipir-administration of 0.1 to 0.2 ml of this formulation per kg body weight—would result in a dose of 1 to 2 μmol/kg mangafodipir and 4 to 8 μmol/kg fodipir.

Calcium has about $10^9$ times lower affinity for fodipir than zinc and about $10^6$ times lower affinity for fodipir than manganese. However, taking in consideration that calcium is present in much higher extracellular concentrations than zinc and manganese, rapid intravenous bolus administration of fodipir may induce acute reduction in the extracellular concentration of free calcium. Since the heart is absolutely dependent on extracellular calcium for its blood pumping activity, reduction in the extracellular content of free calcium may in turn induce acute heart failure. However, as discussed in WO 2011/004325 A1 this problem can be easily solved by making use of the calcium-complexed DPDP, i.e., CaDPDP.

Surprisingly, it has been discovered that CaDPDP may be employed in a complex with manganese in PLED-derivatives. Further, surprisingly, complexes of calcium and manganese, for example, calmangafodipir, and complexes of other Group II metals and Group III-XII transition metals, can be obtained.

Thus, in accordance with one aspect, the invention is directed to a mixed metal complex of a compound of Formula I, or a salt thereof, wherein the mixed metals comprise a Group III-XII transition metal and a Group II metal:

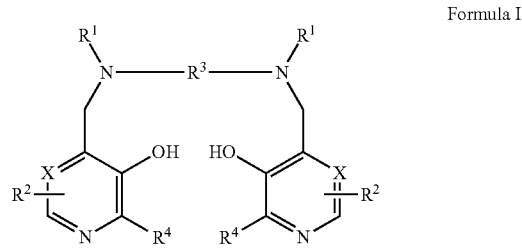

Formula I wherein
X represents CH or N,
each $R^1$ independently represents hydrogen or —CH$_2$COR$^5$;
$R^5$ represents hydroxy, optionally hydroxylated alkoxy, amino or alkylamido;

each $R^2$ independently represents $ZYR^6$ wherein Z represents a bond or a $C_{1-3}$ alkylene or oxoalkylene group, optionally substituted by $R^7$;

Y represents a bond, an oxygen atom or $NR^6$;

$R^6$ is a hydrogen atom, $COOR^8$, alkyl, alkenyl, cycloalkyl, aryl or aralkyl group, optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;

$R^7$ is hydroxy, optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation;

$R^3$ represents a $C_{1-8}$ alkylene, a 1,2-cycloalkylene, or a 1,2-arylene group, optionally substituted with $R^7$; and each $R^4$ independently represents hydrogen or $C_{1-3}$ alkyl.

As used herein the terms "alkyl" and "alkylene" include straight-chained and branched, saturated and unsaturated hydrocarbons. The term "1,2-cykloalkylene" includes both cis and trans cycloalkylene groups and alkyl substituted cycloalkylene groups having from 5-8 carbon atoms. The term "1,2-arylene" includes phenyl and naphthyl groups and alkyl substituted derivatives thereof having from 6 to 10 carbon atoms. Unless otherwise specified, any alkyl, alkylene or alkenyl moiety may conveniently contain from 1 to 20, more specifically 1-8, more specifically 1-6, and even more specifically, 1-4 carbon atoms. Cycloalkyl moieties may conveniently contain 3-18 ring atoms, specifically 5-12 ring atoms, and even more specifically 5-8 ring atoms. Aryl moieties comprising phenyl or naphthyl groups are preferred. As aralkyl groups, phenyl C1-8 alkyl, especially benzyl, are preferred. Where groups may optionally be substituted by hydroxyl groups, this may be monosubstitution or polysubstituition and, in the case of polysubstitution, alkoxy and/or hydroxyl substituents may be carried by alkoxy substituents.

The compound of Formula I may have the same or different $R^2$ groups on the two pyridyl rings and these may be attached at the same or different ring positions. In a specific embodiment, the substitution is at the 5- and 6-positions, or more specifically, the 6-position, para to the hydroxyl group. In a specific embodiment, the $R^2$ groups are identical and identically located, and more specifically are in the 6,6'-positions. In yet more specific embodiments, each $R^6$ is a mono- or poly(hydroxy or alkoxylated) alkyl group or a group of the formula $OP(O)(OR^8)R^7$.

In another embodiment, the invention is directed to a calcium and manganese complex of a compound of Formula I. In one embodiment, $R^5$ is hydroxy, $C_{1-8}$ alkoxy, ethylene glycol, glycerol, amino or $C_{1-8}$ alkylamido; Z is a bond or a group selected from $CH_2$, $(CH_2)_2$, $CO$, $CH_2CO$, $CH_2CH_2CO$ and $CH_2COCH_2$; Y is a bond; $R^6$ is a mono- or poly(hydroxy or alkoxylated) alkyl group or of the formula $OP(O)(OR^8)R^7$; and $R^7$ is hydroxy, or an unsubstituted alkyl or aminoalkyl group. In a more specific embodiment, $R^3$ is ethylene and each group $R^1$ represents —$CH_2COR^5$ in which $R^5$ is hydroxy. In a further embodiment, the compound of Formula I is N,N'-bis-(pyridoxal-5-phosphate)-ethylenediamine-N,N'-diacetic acid (DPDP), or a pharmaceutically acceptable salt thereof. In still further embodiments, the pharmaceutical matter is a mixed manganese and calcium complex of N,N'-bis-(pyridoxal-5-phosphate)-ethylenediamine-N,N'-diacetic acid, or a salt thereof.

The mixed metal complex may include any combination of metals from the indicated Groups. In a specific embodiment, the Group III-XII transition metal is $Mn^{2+}$, $Cu^{2+}$, $Fe^{2+}$ and/or $Ni^{2+}$ and the Group II metal is $Ca^{2+}$ and/or $Mg^{2+}$. In a more specific embodiment, the Group III-XII transition metal is $Mn^{2+}$ and the Group II metal is $Ca^{2+}$ or a mixture of $Ca^{2+}$ and Mg. In more specific embodiments, the Group II metal is a mixture of $Ca^{2+}$ and $Mg^{2+}$ in a $Ca^{2+}/Mg^{2+}$ molar ratio of about 0.1-50, more specifically about 0.1-10.

In further embodiments, the mixed metal complex contains a molar ratio of Group II metal to Group III-XII transition metal of about 1-10. In a specific embodiment, the Group III-XII transition metal is $Mn^{2+}$ and the Group II metal is $Ca^{2+}$ and the molar ratio of $Ca^{2+}/Mn^{2+}$ is about 4. In a more specific embodiment, the Group III-XII transition metal is $Mn^{2+}$ and the Group II metal is $Ca^{2+}$ and the molar ratio of $Ca^{2+}/Mn^{2+}$ is about 4, and the compound of Formula I is DPDP, i.e., the complex is the compound calmangafodipir as described herein.

In another aspect, the invention is directed to a method of producing a mixed metal complex of the invention, in one preparation/crystallization step. The method comprises a one-step crystallization from a solution of the Group III-XII transition metal, the Group II metal, and a compound of Formula I. In a specific embodiment, one-step crystallization from a solution of manganese, calcium, and a compound of Formula I is conducted. In a more specific embodiment, the solution has with a (Ca+Mn)/Mn ratio close to (4+1)/1=5, i.e., with a composition stoichiometry close to $Ca_4Mn(DPDP)_5$.

X-Ray Powder Diffraction (XRPD) is most widely used in the identification and characterization of crystalline solids, each of which produces a distinctive diffraction pattern. Both the positions (corresponding to lattice spacings) and the relative intensity of the lines are indicative of a particular phase and material, providing a "fingerprint" for comparison. As shown in the Examples, an XRPD analysis of calmangafodipir demonstrates without doubt that calmangafodipir is one chemical entity, i.e., a complex, rather than a simple blend, see Example 1. FIG. 1 shows a stacked plot of the three crystalline forms of calmangafodipir which interconvert according to the ambient humidity. Variable humidity XRPD analysis demonstrated Form B to be stable over 40% relative humidity (RH), Form A is stable at 0-10% RH, and Form C is stable between 6-36% RH. Mixtures of Forms B and C were observed between 38-44% RH, and form conversions were observed to occur within 3 hours on a 10 mg scale.

The one step preparation can be performed with or without seeding, but seeding (as exemplified in Example 1) allows for better control of the crystallization.

The above briefly mentioned one step preparation is superior to that of mixing individual metal complexes. Thus, in a specific embodiment, the complex of calcium and manganese is a crystalline material and readily distinguishable from a simple mixture of mangafodipir (MnDPDP) and calfodipir (CaDPDP) in the desirable amounts, as shown in Example 2.

The Examples also show improvements and advantages of the complexes according to the invention, as represented by the calcium-manganese complex calmangafodipir. Regarding the in vivo manganese stability, calmangafodipir is at least as stable as a true mixture of mangafodipir and fodipir, as demonstrated in Example 4. This will result in significantly less retention of manganese in the brain, as demonstrated in Example 8. Since the cytoprotective efficacy mainly depends on the intact manganese complex mangafodipir or its dephosphorylated counterparts, MnDPMP and MnPLED, the efficacy of calmangafodipir is superior to that of mangafodipir, as exemplified in Example 5. Furthermore, mangafodipir has surprisingly been found to possess cytotoxic effects against cancer cells, e.g., CT26 cells (Laurent et al., 2005; Alexandre et al., 2006; EP 16944338). However, as described in WO 2009/078794 A1 and in Kurz et al., 2012, this is an inherent property of fodipir alone or of its dephosphorylated counterparts, DPMP and PLED, and not of the intact metal complex mangafodipir or its dephosphorylated counterparts, MnDPMP and MnPLED. In Example 6 it is shown that fodipir is about 20 times more efficacious than mangafodipir in killing CT26 colon cancer cells, and Example 11 shows that calmangafodipir is about 28 times more efficacious than mangafodipir in killing U1810 non-small cell lung cancer cells. Dissociation to some extent of manganese from fodipir, under in vitro conditions, most probably explains the cancer killing efficacy of mangafodipir. Calmangafodipir as described in Examples 1, 2 and 3, as compared with mangafodipir at manganese equimolar concentrations, is on the other hand as efficacious as fodipir alone, i.e., the killing efficacy of calmangafodipir is much higher than that of mangafodipir at equimolar manganese concentrations. This finding suggests two important properties. Firstly, dephosphorylated PLED is probably as efficacious as its phosphorylated counterpart fodipir with respect to its cancer cell killing ability, and secondly, the lower stability of MnPLED in comparison to that of mangafodipir (Rocklage et al., 1989) probably explains the higher efficacy of MnPLED. The lack of any cytotoxic activity of ZnDPDP and ZnPLED is due to the 1000 times higher stability of these complexes in comparison to their manganese counterparts (Rocklage et al., 1989).

During the development of mangafodipir as an MRI contrast agent, it was discovered that MnDPDP caused fetal skeletal abnormalities in rats but not in rabbits Importantly, this teratogenic effect seen in rats is not caused by intact mangafodipir per se but by dissociated manganese (Grant et al., Acta Radiol. 1997; 38:759-769). Although it is uncertain whether manganese will cause skeletal abnormalities in the human fetus, it is of course essential to protect potentially pregnant women from being exposed to mangafodipir. This represents a minor problem for most clinical applications but a major occupational problem, in particular during the production where costly measures have to be taken in order to protect fertile and potentially pregnant women from exposure to mangafodipir Importantly, the fact that calmangafodipir will release manganese to a much lesser extent than mangafodipir after being accidentally absorbed into the body will of course reduce the risk considerably that a fetus develops skeletal malformations. Secondly, since calmangafodipir is significantly more efficacious than mangafodipir at equimolar doses of manganese, the need of manganese is considerably reduced for every dose of calmangafodipir produced, which will result in less manganese exposure during production.

Furthermore, the preparation of a single active pharmaceutical ingredient reduces the cost of manufacture of a treatment dosage. In addition, the need for dosing of a single material reduces the chance for errors in the formulation of the product. In stability testing, the stability of a crystalline product has been shown to be superior to amorphous material, such as that formed by spray drying a mixture of the two API's. As illustrated in Example 2, amorphous material obtained from spray drying was shown to absorb water rapidly, forming fused particles and/or sticky solids within 24 h exposure at 25° C./60% RH and 40° C./75% RH. In contrast, crystalline calmangafodipir remained a free flowing solid even after 7 days under the same exposure conditions.

It has been discovered, as described in WO 2011/004325 A1, that addition of surplus non-manganese-containing PLED derivative, for example DPDP, to MnPLED-derivative therapy, protects mangafodipir from releasing neurotoxic manganese in vivo. Although the mechanism behind manganese uptake into the brain is not entirely understood, surplus of the non-manganese-containing PLED derivative such as fodipir administered in combination with the manganese-containing PLED derivative such as mangafodipir significantly reduces the uptake of manganese to the brain. While not wishing to be bound by theory, it is believed that the combination according to the invention of WO 2011/004325 A1 maintains the MnPLED chelator form, whereby increased amounts of chelates are available for excretion and the amount of free Mn for uptake into the brain and other organs is reduced. Low molecular weight manganese chelates, like MnPLED-derivatives, and their Zn-counterparts will readily be excreted through the kidney, governed by the glomerulus filtration rate (GFR), whereas manganese not bound to a low molecular weight chelator will be retained for quite a while in the body and excreted slowly and mainly via the biliary route (Toft et al., 1997). As shown in the following Example 8 herein, repeated (39 times over 3 months) intravenous injections of a high dose (36 times the assumed clinical assumed dose) of calmangafodipir into rats caused significantly less retention of manganese in the brain, compared to that caused by mangafodipir. The total dose in both cases corresponded to approximately 2800 μmol/kg of manganese. This example also shows that the pancreas takes up and retains dissociated manganese to a relatively large extent, a property previously described by Ni et al. (Acta Radiol 1997; 38:700-707) and utilized as a promising diagnostic MRI method of the pancreas (Ahlström et al, Acta Radiol 1997; 38:660-664). The significantly lower manganese level in the pancreas of calmangafodipir-treated rats in comparison to those treated with mangafodipir further confirms the improved toxicological profile of calmangafodipir. Although, the Mn content of the liver was statistically significant elevated in the mangafodipir group, the relative elevation was much less than those in the brain and pancreas. A single diagnostic dose of mangafodipir (5 μmol/kg b.w.) is known to cause rapid increase in the Mn content of both the pancreas and the liver of rats—after 2 hours the Mn content of the pancreas was approximately 10 times higher than the basal value, and the corresponding value of the liver was increased about 2 times (Ni et al., 1997). Whereas Ni et al found the Mn content still elevated after 24 hours in the pancreas (about 5 times the basal value), it was back to baseline in the liver at that time point. This presumably reflects the high capacity of the liver to handle manganese and its important physiological role in manganese homeostasis. This is further supported by the present results showing just a modest increase in liver Mn after heavy exposure to mangafodipir. The improved toxicological profile of calmangafodipir is clearly illustrated by Example 8 herein.

When a clinical dose of a MnPLED-derivative such as mangafodipir (i.e., 5-10 μmol/kg b.w., intravenous administration) is used as an MRI contrast agent in a human, about 80% of the manganese bound to fodipir (DPDP) is exchanged with zinc (Toft et al., 1997). As smaller doses of mangafodipir are administered, the percentage of manganese which dissociates will be even greater. Mangafodipir behaves in that perspective in a similar manner in rats and dogs (Hustvedt et al., 1997); however, almost all manganese in mangafodipir is exchanged for zinc when the compound is administered into pigs and is hence without cytoprotective effects in pigs (Karlsson et al., 2001). On the other hand, administration of low doses of MnPLED causes profound cytoprotective effects in pigs, seen as a significantly reduced myocardial infarct size upon ischemia-reperfusion. Although the reported stability constant between $Mn^{2+}$ and PLED is considerably lower than the corresponding figure for $Mn^{2+}$ and fodipir (Rocklage et al., 1989), MnPLED for some unknown reason escapes metal exchange. Displacement of manganese is a prerequisite and therefore desirable for use as an MRI contrast agent, e.g., for liver and pancreas diagnostic purposes. However, the SOD-mimetic therapeutic effect against various forms of oxidative stress depends fully on the intact manganese PLED-derivative complex (Brurok et al., 1999; Karlsson et al., 2001). For example, whereas in vivo administration of mangafodipir protects against various oxidative stressors, e.g., ischemia-reperfusion, cytotoxic/cytostatic drugs and acetaminophen intoxication, it does not protect the pig heart against ischemia-reperfusion-induced myocardial infarction (Karlsson et al., 2001), results from which it can be concluded that the in vivo cytoprotective effects of MnPLED-derivatives are an inherent property of the intact manganese complex.

The presence of Ca in an approximately 4 times excess to Mn, as in calmangafodipir, profoundly stabilizes the complex or its dephosphorylated counterparts from releasing manganese after injections and thus provides another important advantage, namely increased therapeutic efficacy. For example, when a clinically relevant imaging dose of MnDPDP (5-10 µmol/kg) is intravenously injected, about 80% of the manganese originally bound to DPDP is released, contributing to the imaging efficacy. Consequently less than 20% remains bound to DPDP or its dephosphorylated counterparts, contributing to the therapeutic activity of MnDPDP. As the release of manganese from the complex can be effectively reduced by an approximately 4 times excess of Ca, in comparison to Mn, in calmangafodipir, this means that manganese can be reduced considerably for an equipotent therapeutic effect, as clearly exemplified in the present invention. At lower and, in certain embodiments, more therapeutic relevant doses, the stabilizing effect of Ca will even be more accentuated. This, in turn, means that the use of calmangafodipir in comparison to mangafodipir will have profound effects on the neurotoxic potential—both as a result of an in vivo stabilizing effect and as a result of increased therapeutic efficacy of the new pharmaceutical matter calmangafodipir, with a composition stoichiometry close to $Ca_4Mn(DPDP)_5$.

Zinc is present in all body tissues and fluids. The total body zinc content in humans has been estimated to be 2-3 g (Folin et al., BioMetals 1994; 7:75-79). Plasma zinc represents about 0.1% of total body zinc content, and it is mainly this small fraction of zinc that competes with manganese for binding to fodipir or its dephosphorylated counterparts, DPMP and PLED, after administration. The human body has a very high capacity to maintain zinc homeostasis through synergistic adjustments in gastrointestinal absorption and excretion (King et al., J Nutr 2000; 130:1360S-1366S).

While not wishing to be bound by theory, from preclinical work (Southon et al., 1997) and from clinical work (Skjold et al., 2004), it may be reasonable to assume that the body contains 5 to 10 µmol/kg body weight (b.w.) zinc that is readily exchangeable for manganese in a MnPLED-derivative such as mangafodipir. This substantially corresponds to the zinc content of the plasma as described above. The PLED-derivatives such as fodipir contain one binding site for manganese/zinc per molecule. Thus, in view of the 1000 times higher affinity for zinc to the chelator, the presence of calcium in calmangafodipir at a ratio of around 4 in comparison to manganese will protect against release of manganese after parenteral administration to a patient.

In another embodiment, the invention is directed to methods for treatment of a pathological condition in a patient, including, but not limited to, a pathological condition caused by the presence of oxygen-derived free radicals, i.e., oxidative stress, by administration of the complex. In a specific embodiment, the pathological condition is caused by superoxide resulting in subsequent lipid peroxidation and/or protein nitration. In a specific embodiment, the complex may be administered for therapeutic treatment of such a pathological condition in a human patient or another mammal. In another specific embodiment, a complex according to the invention is administered for treatment of a pathological condition caused by the presence of oxygen-derived free radicals, i.e., oxidative stress, in a mammal.

In one embodiment, the complex is employed in cytotoxic or cytostatic drug treatment, wherein the complex is administered to provide protection from disadvantageous side effects of the cytotoxics/cytostatic drugs, for example, one or more cancer drugs in cancer patients. In a more specific embodiment, the cytotoxic or cytostatic drug comprises at least one of doxorubicin, epirubicin, oxaliplatin, carboplatin, cisplatin, 5-fluorouracil, docetaxel or paclitaxel. In additional embodiments, the pathological condition is myeolosuppression or neurotoxicity, or both.

The methods according to the invention may also include, but are not limited to, treatment of acetaminophen-induced liver failure, non-alcoholic steatohepatitis (NASH), viral-induced chronic hepatitis, Wilson's disease, diabetes, ischemic heart disease, including ischemia-reperfusion-induced injury, or myocardial ischemia-reperfusion-induced injury, both in an acute as well as elective setting, a condition associated with a thrombolytic treatment, a cardiopulmonary bypass, or percutaneous transluminal angioplasty, or is a result of cardiac or organ transplantation surgery or stroke. In additional embodiments, the methods according to the invention may also include treatment of iron-related conditions, including iron overload, for example, thalassemia, sickle cell anemia or transfusional hemosiderosis, hepatitis-induced liver cirrhosis, radiation induced injury, for example, resulting from radiation therapy, various neurodegenerative diseases, including Alzheimer's disease, amyotrophic lateral sclerosis (ALS), Parkinson's disease, and multiple sclerosis, and the like.

In yet further embodiments, the methods according to the invention are administered as replacement therapy for a pathological condition of low manganese superoxide dismutase (MnSOD) activity, such as occurs in various forms of cancer (Buettner, Anticancer Agents Med Chem. 2011; 11:341-346). Thus, in one embodiment, the invention is directed to a method for the treatment of non-small cell lung cancer by administering the complex of the invention, or, more specifically, calmangafodipir. In additional embodiments, the invention is directed to a method for the treatment of colorectal cancer, prostate cancer, breast cancer, pancreatic cancer, or malignant melanoma, by administering the complex of the invention, or, more specifically, calmangafodipir.

An interesting and probably important property for the antitumor effect of mangafodipir may be its lymphocyte protecting property, as shown in Example 5, and by Laurent et al., 2005 and Alexandre et al., 2006. Although inflammatory processes secondary to oxidative stress damage normal tissue, they may in fact be beneficial to tumor tissue by creating growth factor-rich microenvironment and promoting growth of cancerous clones (Anscher, Onclogist 2010; 15:350-359; Kareva, Transl Oncol 2011; 4:266-270; Kerkar et al., Cancer Res 2012; 72:3125-3130). A striking example is the existence of tumor-associated macrophages that accumulate preferentially in the poorly vascularized regions of tumors and secrete cytokines that actually promote tumor growth. Moreover, not only can these cytokines promote tumor growth but they have also been shown to suppress activation of CD8+ T-lymphocytes that are most efficient in tumor elimination. In fact, there is an increasing interest for the importance of T-lymphocyte-mediated immune response for the outcome of cancer chemotherapy (Zitvogel et al., Nat Rev Clin Oncol 2011; 8:151-160; Kerkar et al., 2012). It is known that severe lymphopenia (<1000 cells/µl) negatively affects the chemotherapy response. A collection of mouse cancers, including CT26 colon cancer, MCA205 fibrosarcomas, TSA cell-line breast cancers, GOS cell-line osteosarcomas and EL4 thymonas, respond to chemotherapy with doxorubicin and oxaliplatin much more efficiently when they are implanted in syngenic immune-competent mice than in immune-deficient hosts, i.e., nude mice (Zitvogel et al., 2011). This is in line with clinical studies revealing that IFN-γ-producing CD8+ T-lymphocytes are potent cancer immune effectors. Furthermore, a high neutrophil/lymphocyte ratio is associated with a low overall survival for patients with advanced colorectal cancer (Chua et al., Br J Cancer 2011; 104:1288-1295). Taking into consideration that mangafodipir and in particular calmangafodipir are highly efficient lymphocyte-protecting agents during chemotherapy, it is plausible that this property is of particular importance during in vivo conditions.

To be clinically useful, a chemotherapy protectant or a radiotherapy protectant used in cancer patients should fulfill three criteria: (i) the agent should protect normal tissue from chemotherapy/radiotherapy-induced toxicity but not protect tumor tissue (at least not to any greater extent)—otherwise no benefit will be obtained; (ii) the agent should be delivered with relative ease and with minimal toxicity; and (iii) the agent should protect normal tissues against dose-limiting toxicities or those responsible for significant reduction in quality of life (Citrin et al., 2010). The compounds of the invention, and calmangafodipir in particular, fulfill all these criteria, as the examples herein demonstrate. The reason why mangafodipir and calmangafodipir protect nonmalignant cells but damage cancer cells is seemingly a paradox. While not wishing to be bound by theory, it may, however, be that protection of nonmalignant cells and cytotoxic actions against cancer cells just are two sides of the same coin. An elevated oxidative status is indispensable for mitogenic stimulation in transformed cells (Irani et al., Science 1997; 275:1649-1652). A number of studies have reported that reactive oxygen species (ROS) play an important role in promoting tumor metastasis (e.g., Behrend et al., Mol Cell Biol 2005; 25:7758-7769). These data are consistent with a large body of literature suggesting that the redox balance of many epithelial tumor cells favors an elevated oxidant set point (Doroshow, 2006), including CT26 cells (Laurent et al., 2005; Alexandre et al., 2006). MnSOD suppresses cell growth in a variety of cancer cell lines and in mouse models. Furthermore, overexpression of MnSOD induced growth arrest in the human colorectal cancer cell line HCT116 and increased senescence that required the induction of p53 (Behrend et al., 2005). Introduction of the normal MnSOD gene in cancer cells alters the phenotype and the cells lose their ability to form colonies in culture and tumors in nude mice (Church et al., Proc Natl Acad Sci USA 1993; 90:3113-3117). The elevated oxidative status seen in cancer cells typically leads to increased production of $.O_2^-$ which readily reacts with .NO to form highly toxic $ONOO^-$ resulting in tyrosine nitration, the "ugly" side of .NO (Beckman et al, 1996; Radi, 2004). Interestingly, convincing evidence suggests that tyrosine nitration is involved in the above described suppression of CD8+ lymphocyte mediated immunological response in tumors of (Bronte et al., J Exp Med 2005; 201, 1257-1268; Molon et al., J Exp Med 2011; 208:1949-1962). It may be that calmangafodipir through its SOD mimetic activity inhibits $ONOO^-$ production and hence the immunological suppression, explaining the increased antitumor effect seen in immune competent mice but not immune incompetent mice, as demonstrated by Example 10. Peroxynitrite is not capable of protein nitration directly but typically needs a redox active transition metal like iron or copper (and even manganese may fulfill this need) (Radi, 2004). Fodipir and its dephosphorylated metabolites have an extremely high affinity for $Fe^{3+}$ (Rocklage et al., 1989). This property may, in addition to the SOD mimetic activity of calmangafodipir, be of a particular importance for the antitumor activity. In addition to the T-lymphocyte-dependent action, the direct immune-independent action of DPDP and PLED, can be due to inhibition of topoisomerase II, as a recent paper of Kurz (2012) may suggest.

The complex may be administered in a pharmaceutical composition. Optionally, the pharmaceutical compositions of the present invention may include one or more physiologically acceptable carriers and/or excipients, in a manner well-known to those skilled in the art. In one embodiment, the complex may for example be suspended or dissolved in a liquid medium, optionally with the addition of pharmaceutically acceptable excipients. Suitable excipients for the pharmaceutical compositions include any conventional pharmaceutical or veterinary formulation excipients, including, but not limited to, stabilizers, antioxidants, osmolality adjusting agents, buffers, pH adjusting agents, binders, fillers, and the like. The pharmaceutical compositions may be in a form suitable for administration, including both parenteral and enteral administration. In a specific embodiment, the composition is in a form suitable for example injection or infusion. Thus, the pharmaceutical compositions of the present invention may be in a conventional pharmaceutical administration form such as a tablet, capsule, powder, solution, suspension, dispersion, syrup, suppository, aerosol, ointment, plaster, or the like. In a further embodiment, the complex is in freeze dried form and, if desired, may be reconstituted prior to administration. The freeze dried complex may be in a freeze dried composition containing one or more stabilizers, and/or other excipients known for use in freeze drying.

Such compositions according to the present invention may be administered by various routes, for example orally, transdermally, rectally, intrathecally, topically or by means of inhalation or injection, in particular subcutaneous, intramuscular, intraperitoneal or intravascular injection. Other routes of administration may be used as well, including intratympanic and intranasal, and routes which increase the effectiveness, the bioavailability or the tolerance of the products are preferred. The most appropriate route can be chosen by those skilled in the art according to the particular formulation which is used. Suitable dosages will be apparent relative to the selected treatment. In one embodiment, the treatment method according to the invention comprises administering about 0.01 to 50 µmol/kg body weight of the mixed metal complex. In more specific embodiments, the treatment method according to the invention comprises administering about 0.1 to 10 µmol/kg, or about 0.1 to 5 µmol/kg, body weight of the mixed metal complex.

The following examples demonstrate various embodiments and aspects of the invention.

Example 1

Method

A jacketed 100-L reactor—flushed with $N_2$—was charged with fodipir (DPDP) (4.0 kg anhydrous based, 6.27 mol, 1 equiv) and deionized (DI) water (19.2 L, 4.88 vol). The pH of the batch was adjusted to 5.7 with dilute NaOH (8.9 L total, 17.5 mol NaOH, 2.8 equiv; prepared from 1.41 kg of 50 wt %

NaOH and 8.0 L of DI water) over 35 min (21.0-23.3° C.; external cooling). The slurry was stirred for 1 h at 20-25° C. during which time a solution formed. To this was sequentially charged Ca(OH)$_2$ (361.1 g, 4.87 mol, 0.78 equiv), L-ascorbic acid (55.1 g, 0.313 mol, 5 mole %), and MnO (80 g, 1.13 mol, 0.18 equiv). After the addition of each reagent the batch was stirred for 30-60 min at 20-25° C. and the pH was measured (after Ca=6.24, slight cloudy pale yellow to rust; after ascorbic=6.28 less cloudy rust; after Mn=6.38, cloudy rust to yellow-green). The cloudy batch was stirred for 16 h at 20-25° C., pH was measured (6.36) and the batch was filtered through a 0.3µ in-line filter into a clean 100-L reactor. Meanwhile, an ethanol (EtOH) 23 A solution was prepared with acetone (5.9 L, 1.47 vol) and EtOH (74 L, 18.5 vol). A portion of the EtOH 23 A solution (8.0 L, 2 vol) was charged to the batch over 30 minutes at 20-25° C. during which time the solution became cloudy. The batch was seeded with calmangafodipir (40 g, 1 wt %) and stirred for 30 min at 20-25° C. to ensure solids persisted.

The batch temperature was adjusted to 15° C. over the course of 1 h and then aged for 30 min at 13.8-15.5° C. To the batch was charged EtOH 23 Å (56 L, 14 vol) over 10 h (11-14° C.). The slurry was mixed for 13 h at 5-10° C. and then filtered to collect the solids. The reactor and solids were rinsed with chilled (0-10° C.) EtOH 23 Å (14 L, 3.5 vol), the solids were conditioned for 2 h and then dried in a vacuum oven at 45° C. for 72 h to afford 4.819 kg (93% yield adjusted for water content) of calmangafodipir (lot #11AK0105B) as a yellow solid. HPLC analysis showed a purity of 98.8%. Oven Karl Fisher analysis (@170° C.) showed 10.1% water. ICP analysis indicated 4.27% Ca, 1.37% Mn, 8.64% Na for a Ca/Mn ratio of 4.27, i.e. with a composition stoichiometry close to Ca$_4$Mn(DPDP)$_5$.

Results

XRPD (X-Ray Powder Diffraction) analysis was conducted and the resulting patterns are shown in FIG. 1. The XRPD patterns demonstrate that calmangafodipir is a single chemical entity rather than a simple blend. FIG. 1 shows a stacked plot of the three known crystalline forms of calmangafodipir which interconvert according to the ambient humidity. Variable humidity XRPD analysis demonstrated Form B to be stable over 40% RH, Form A stable at 0-10% RH, and Form C stable between 6-36% RH. Mixtures of Forms B and C were observed between 38-44% RH, and form conversions were observed to occur within 3 hours on a 10 mg scale.

Conclusion

The XRPD demonstrated surprisingly calmangafodipir as being one chemical entity rather than a simple blend (FIG. 1).

Example 2

Method

In a 4:1 ratio approximately 200 mg of calfodipir (CaDPDP) and 50 mg of mangafodipir (MnDPDP) were weighed into a 40 mL vial and dissolved in 40 mL of DI water at room temperature to generate a yellow solution. The yellow aqueous solution was spray dried using a Buchi Mini-Spray Dryer B-290 while attached to the Buchi dehumidifier B-296 as an air conditioner allowing the intake of air from the laboratory. Spray drying optimization experiments were performed at elevated inlet temperatures (220° C.) with varying feed rates (20, 30, 40, 50 and 60%). Recovery of product ranged from 180-230 mg.

Results

Figure 2:
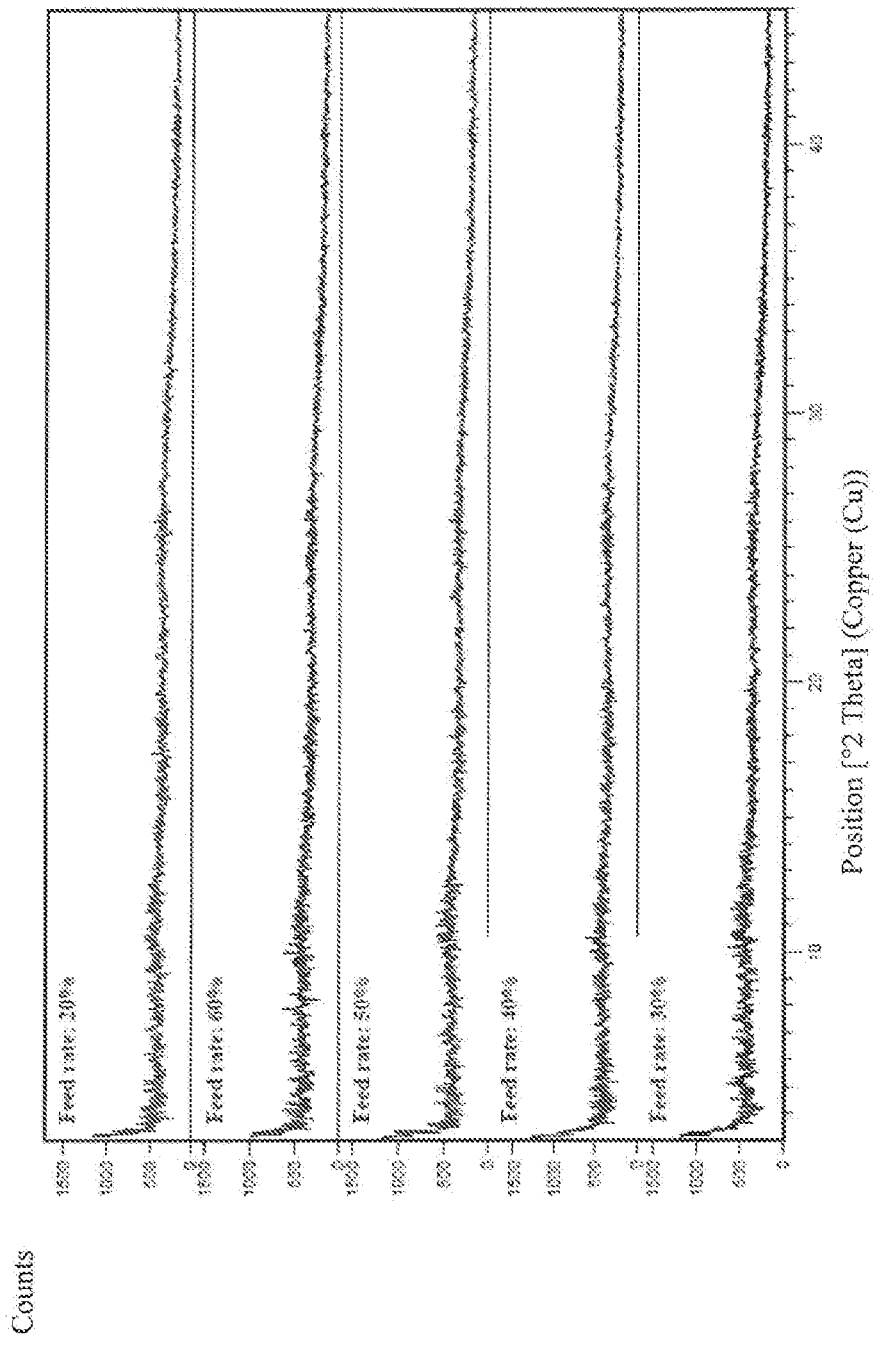
FIG. 2 shows XRPD patterns of mixtures of calcium fodipir (calfodipir) and manganese fodipir (mangafodipir), rather than a complex according to the invention; these XRPD patterns indicate all products were amorphous and were shown to absorb water rapidly, as described in Example 2.

The resulting materials were analyzed by XRPD (FIG. 2) which indicated all products were amorphous and were shown to absorb water rapidly, forming fused particles and/or sticky solids within 24 h exposure at 25° C./60% RH and 40° C./75% RH.

Example 3

This example elucidates the structure of the new chemical entity calmangafodipir by making use of: Infrared Absorption Spectroscopy; Mass Spectroscopy; and Elemental Analysis. NMR analysis cannot be utilized for analysis of calmangafodipir due to the paramagnetic nature of Mn.

Methods

The analyses described in this example were conducted on a product produced according to the one step method described herein. The product is identified as lot#7755-C-R0-01-30-01, and was prepared essentially as described in Example 1. A portion of this product has been certified as a reference standard for calmangafodipir.

Infrared Absorption Spectroscopy.

The Fourier transform infrared (FT-IR) absorption spectrum of calmangafodipir, lot #7755-C-R0-01-30-01 was obtained using attenuated total reflection (ATR) on a Thermo-Nicolet Avatar 370 spectrometer.

Mass Spectroscopy.

The mass spectrum of calmangafodipir, lot #7755-C-R0-01-30-01, was acquired on a Waters Q-Tof Micro MS/MS system. Electrospray Ionization (ESI) (positive ion polarity mode) was chosen for the MS analysis. The sample was dissolved in a solution of 50:50 Acetonitrile/Water+0.1% Formic Acid at a concentration of 10 µg/mL. The solution was infused directly into the source at a rate of 10 µL/minute.

Elemental Analysis.

Calmangafodipir lot #7755-C-R0-01-30-01 was manufactured using a Ca/Mn molar ratio of 4.26 and 2.8 mol Na/mole of fodipir. The theoretical metals content of the complex with this composition is 1.41% Mn, 4.38% Ca, and 8.69% Na.

Results

Figure 3:
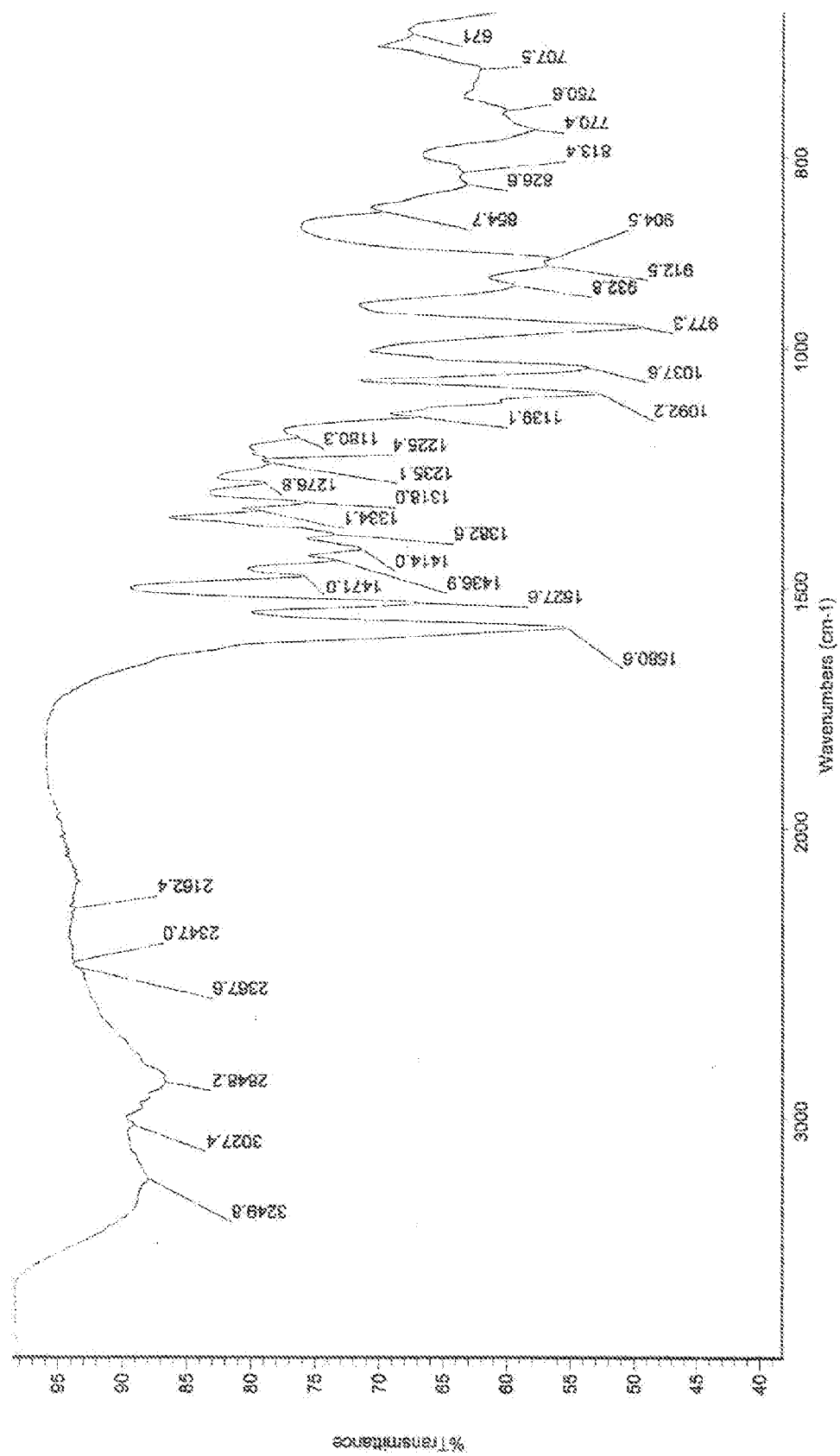
FIG. 3 shows the Fourier transform infrared (FT-IR) absorption spectrum of calmangafodipir, lot #7755-C-R0-01-30-01, with the characteristic infrared absorption bands (wave number) and the corresponding assignments described in Example 3.

The infrared absorption spectrum is shown in FIG. 3, and the characteristic infrared absorption bands (wave number) and the corresponding assignments are as follows:

| Wave number (cm$^{-1}$) | Assignment |
|---|---|
| 3250 | N—H |
| 3027-2848 | C—H |
| 1581 | C=O |
| 1528 | C=C |
| 1471, 1437 | CH$_2$, CH$_3$ |
| 1383 | CH$_3$ |
| 1277 | P=O |
| 1092 | P—OH |
| 1038, 977, 933, 913 | P—O—C |
| 827, 813, 770, 751 | Aromatic C—H |

Figure 4A:
FIGS. 4A and 4B show mass spectrum (FIG. 4A) and expanded mass spectrum (FIG. 4B) of calmangafodipir, lot #7755-C-R0-01-30-01 (660-850 m/z), as described in Example 3.
Figure 4B:
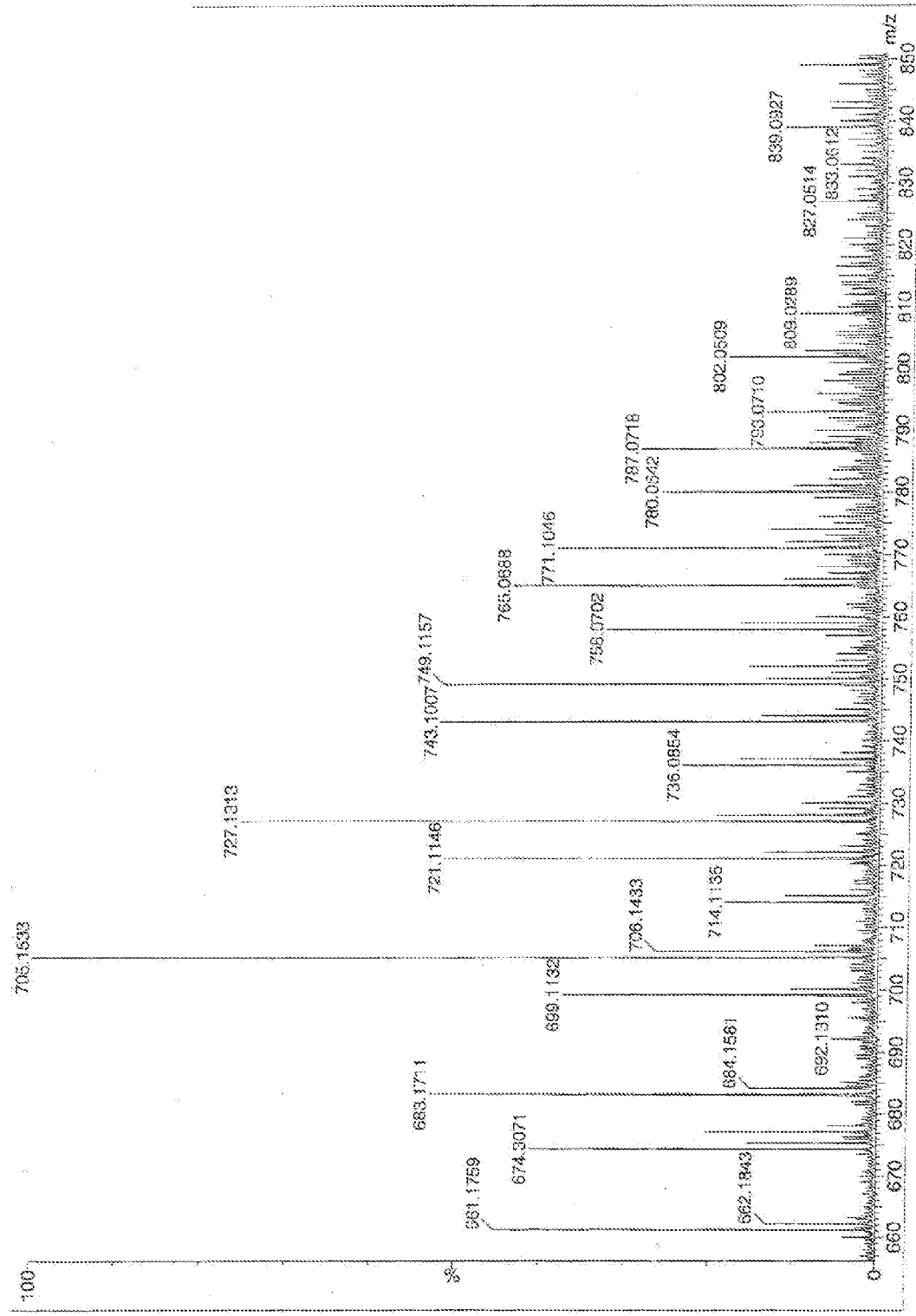

The mass spectrum and an expanded mass spectrum of the sample are shown in FIGS. 4A and 4B, respectively. The spectrum presents as that of calfodipir and mangafodipir superimposed on each other. The exact mass of fully protonated calfodipir is 676 and a mass of 677 for [M+1] is observed. The exact masses for monosodium, disodium, trisodium, and tetrasodium are 698, 720, 742, and 764, respectively. The spectrum shows [M+1] for each species at 699, 721, 743, and 765, respectively. The exact mass of fully protonated Mangafodipir is 691, with the corresponding monosodium, disodium trisodium, trisodium, and tetrasodium species at 713, 735, 757, and 779, respectively. The spectrum exhibits masses at 692, 714, 736, 758, and 780 for [M+1] for each species.

The metals content results for lot#7755-C-R0-01-30-01 were 1.48% Mn, 4.44% Ca, and 8.56% Na and are in agreement with the expected values, confirming that both the manganese and calcium are complexed, with sodium as the counterion, and that little or none of the calcium is present simply as a counterion.

Conclusion

Figure 5:
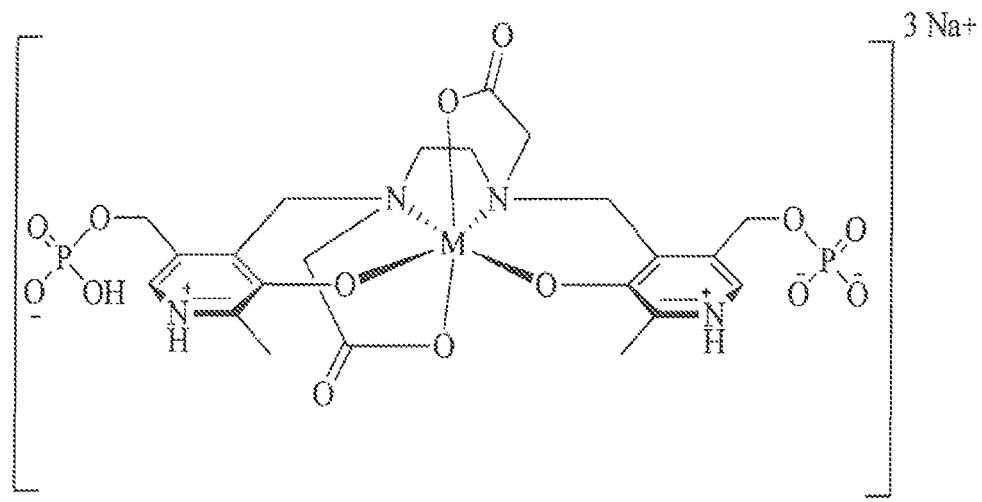
FIG. 5 shows the chemical structure of calmangafodipir, as described in Example 3.

These results are consistent with the structure shown in FIG. 5. FIG. 5 shows the ideal and generic 4:1 Ca/Mn with 3 Na as counterions, which gives the molecular weight of 745.43 shown in FIG. 5. The average molecular weight for material prepared as described and studied in this Example has a 4.26 Ca/Mn ratio and 2.8 Na as counterions, having a molecular weight of 740.89.

Example 4

This example measured manganese (Mn) and zinc (Zn) urine excretion in animals receiving calmangafodipir or mangafodipir, at Mn equimolar doses.

Method

Eight male Wistar rats (approximately 250 g) were injected intravenously, via one of the tail veins, with 0.25 ml of a 50 mM calmangafodipir (lot #11AK0105B) solution, containing approximately 10 mM Mn and 40 mM Ca, or 0.25 ml 10 mM mangafodipir (lot #02090106), containing 10 mM Mn. After injection, the rats were immediately placed in metabolic cages for urine collection over a period of 0-24 hours. To obtain basal content of manganese (Mn) and zinc (Zn) in urine, two additional (control) rats received 0.25 ml saline and were placed in metabolic cages for urine collection over the same period of time. The urine samples were then stored at −80° C. until Mn analysis. Before analysis, the samples were thawed and extensively shaken to obtain homogenous samples. A five ml aliquot was taken from each sample and 5 ml concentrated nitric acid was added. The samples were then resolved in a microwave oven and thereafter diluted with distilled water to a final volume of 50 ml. The Mn content of each sample was analyzed by ICP-MS (Inductively Coupled Plasma Mass Spectrometry). Identical samples of calmangafodipir and mangafodipir as those injected in the rats (i.e., 0.25 ml) were withdrawn and injected into test tubes. These samples were treated in an identical manner to that of the urine samples and analyzed for their Mn content. Results are presented as total 0-24 h urine Mn content (expressed as μmol/kg±S.E.M.) and as percentage (±S.E.M.) of the injected dose. The statistical difference between animals receiving calmangafodipir and mangafodipir, with respect to excretion of manganese into the urine, was tested by an unpaired Student's t-test. A p-value lower than 0.05 was considered as a statistically significant difference.

Results

Results are set forth in FIGS. 6A, 6B and 6C. Twenty-four hours after iv injection of 0.25 ml 10 mM mangafodipir containing 2.59 μmol manganese (Mn), 0.60±0.04 μmol Mn was recovered in urine (FIG. 6A), corresponding to 23.1±1.4% of the injected dose (after the basal excretion of 0.035 μmol has been subtracted, FIG. 6B). The corresponding figure after injection of 0.25 ml 50 mM calmangafodipir containing 2.52 μmol Mn was 1.27±0.07 μmol Mn (FIG. 6A), corresponding to 50.5±2.6% of the injected dose (FIG. 6B). The difference between mangafodipir and calmangafodipir was highly significant (p<0.0001). The difference in renal Mn excretion was more or less reflected in the difference in renal excretion of zinc (Zn); expressed as increased Zn excretion, i.e., the basal 24 h excretion (0.068 μmol) is subtracted (FIG. 6C).

Conclusion

Thus, at an equivalent Mn dose, calmangafodipir doubled Mn excretion in urine in comparison to mangafodipir. The percentage Mn excreted in urine during 0-24 h after intravenous injection of mangafodipir corresponds very well with previously reported figures in rats (Hustvedt et al., 1997) and humans (Toft et al., 1997). The present results demonstrate that calmangafodipir releases much less Mn under in vivo conditions than mangafodipir. This provides significant advantages in that the amount of free Mn available for uptake by the brain and other organs is reduced and that the therapeutic index is significantly increased as more of therapeutic mangafodipir or its dephosphorylated counterparts, MnDPMP and MnPLED, are available in vivo. Thus, calmangafodipir renders a therapeutic treatment considerably less toxic and much more efficacious than that of mangafodipir.

Example 5

This example compares the cytoprotective effect of calmangafodipir with that of mangafodipir and MnPLED with respect to myelosuppressive effects of oxaliplatin in balb/c mice.

Method

In a first series of experiments, 3 groups each consisting of 5 female balb/c mice were treated once intraperitoneally with oxaliplatin at 7.5, 10.0 and 12.5 mg/kg oxaliplatin, respectively. One day before (baseline) as well as 3 and 6 days after oxaliplatin treatment 50 μl EDTA blood samples were taken from the orbital venous plexus with a glass capillary. The blood samples were analyzed using the automated system CELL-DYN® Emerald (Abbott Diagnostics) for the content of white blood cells (WBC), lymphocytes (LYM), neutrophils (NEU) and platelets (PLC). From the results (FIGS. 7A-7D) it was concluded that further experiments testing the myeloprotective effects of calmangafodipir, mangafodipir and MnPLED should be performed at 12.5 mg/kg oxaliplatin and that blood cell sample analyses should be performed the day before and 6 days after oxaliplatin administration in every mice. Thirty minutes before administration of oxaliplatin (12.5 mg/kg) and 24 hours after, the mice received saline, calmangafodipir (5 mg/kg; lot #11AK0105B), mangafodipir (1 and 10 mg/kg; lot #02090106) or MnPLED (1 mg/kg), intravenously (5 mice in each group). A dose of 5 mg/kg calmangafodipir contained the same amount of manganese as that of 1 mg/kg mangafodipir, i.e., 1.3 μmol; 1 mg/kg of MnPLED contained somewhat more manganese (approximately 2 μmol). A control group received instead of oxaliplatin vehicle (5% glucose) and saline. The results are presented in graphs as relative changes from baseline for the various treatments and blood cells (±S.E.M.). The statistical differences between treatment groups, where appropriate, were tested by an unpaired Student's t-test. A p-value lower than 0.05 was considered as a statistically significant difference.

Results

Figure 7A:
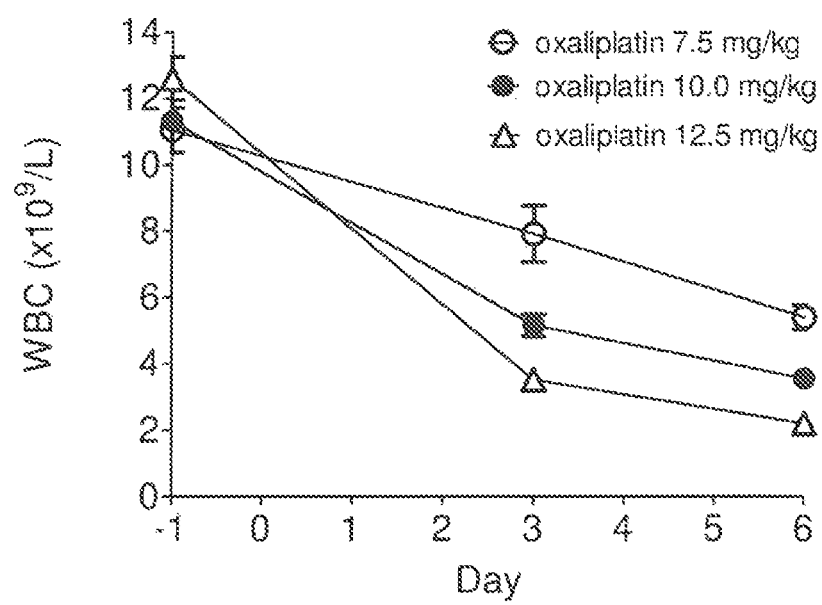
FIGS. 7A-7D show the myelosuppressive effects on white blood cells (WBC), lymphocytes (LYM), neutrophils (NEU), and platelets (PLC), respectively, of single intravenous injection of increasing doses (7.5, 10.0 and 12.5 mg/kg) of oxaliplatin at 3 and 6 days post injection. Results expressed as mean±S.E.M.; n=5 in each group, as described in Example 5.
Figure 7B:
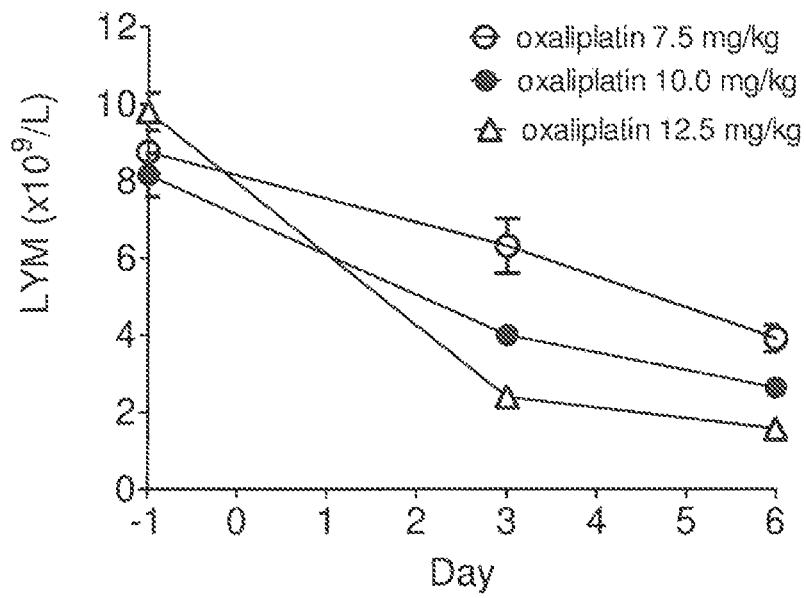
Figure 7C:
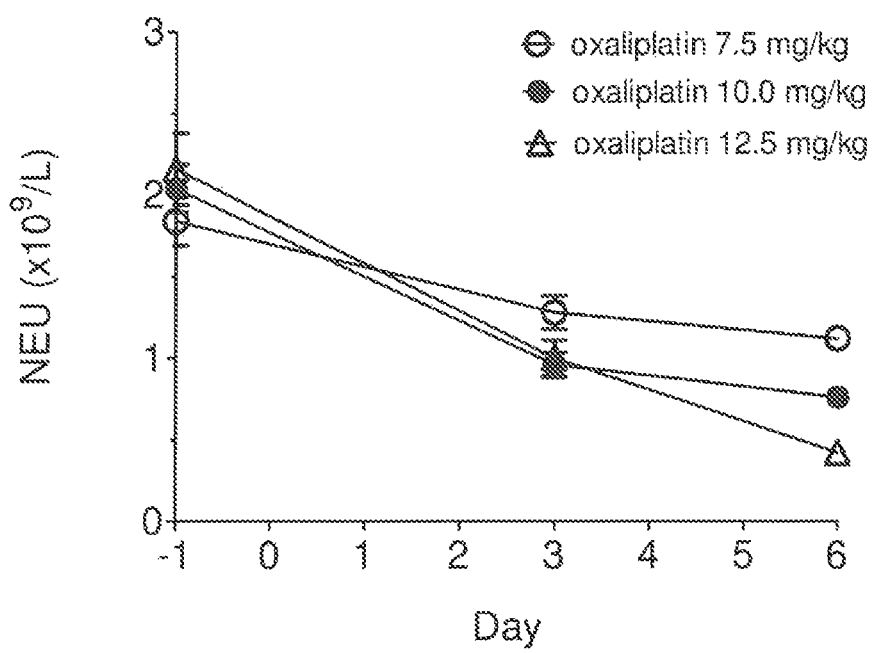
Figure 7D:
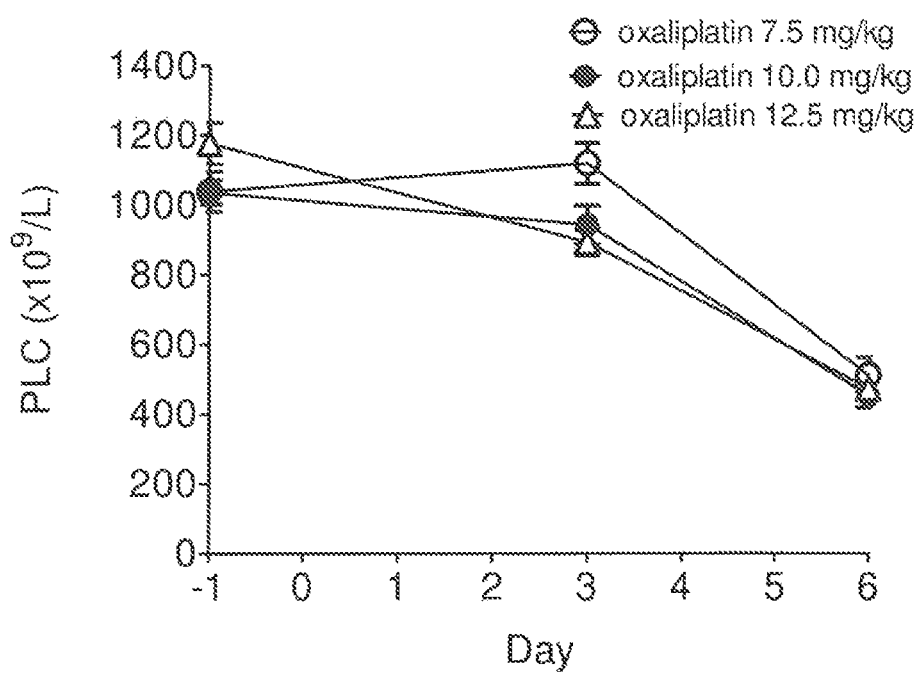
Figure 8A:
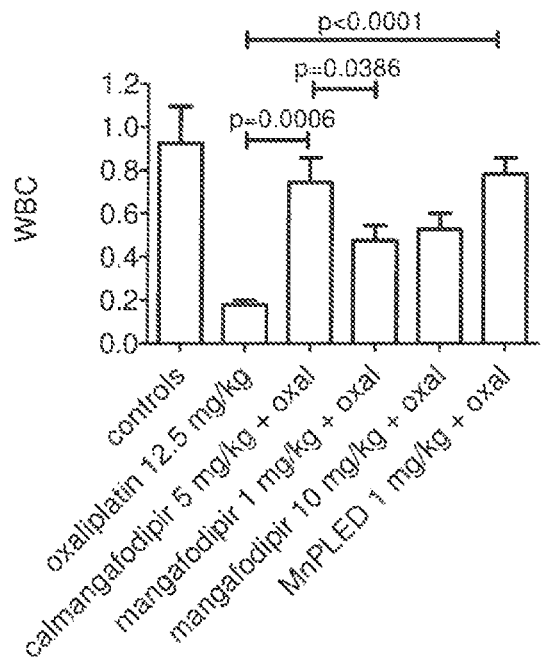
FIGS. 8A-8D show WBC, LYM, NEU and PLC, respectively after oxaliplatin treatment alone or in combination with calmangafodipir or mangafodipir in balb/c mice. Controls received vehicle treatment only. Results expressed as mean±S.E.M.; n=5 in each group, as described in Example 5.
Figure 8B:
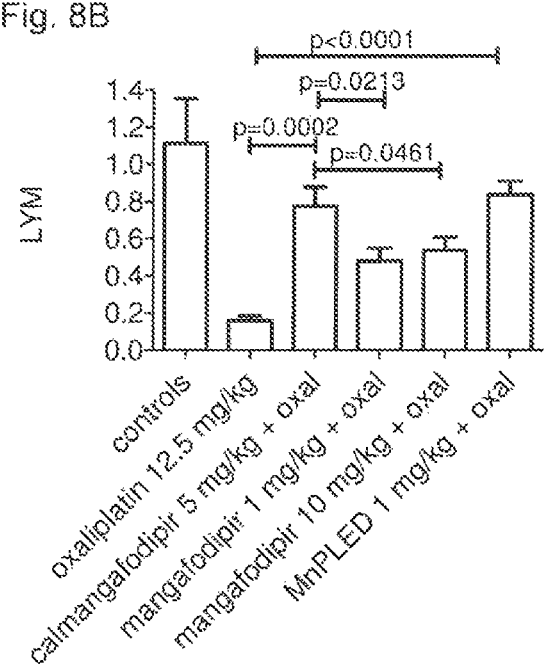
Figure 8C:
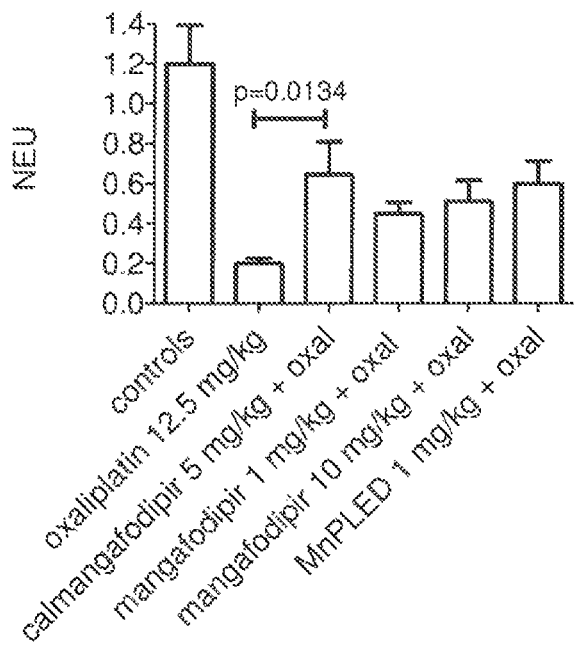
Figure 8D:
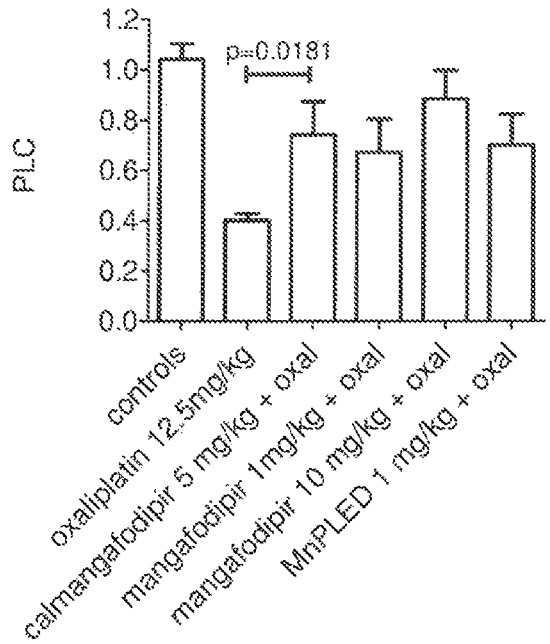

The results are set forth in FIGS. 8A-8D. At an equivalent manganese dose, i.e., 5 mg/kg calmangafodipir was statistically significant more efficacious than 1 mg/kg mangafodipir to protect the mice from oxaliplatin-induced fall in total number of white blood cells (WBC) (FIG. 8A). A single dose of 12.5 mg/kg oxaliplatin caused the WBC to fall more than 80%, whereas the fall in animals treated with calmangafodipir was only about 25%. The corresponding fall in mice treated with 1 or 10 mg/kg mangafodipir was around 50%. These results presumably also suggest that MnDPDP has to be dephosphorylated into MnPLED before it can exert myeloprotective effects; 1 mg/kg MnPLED was, like calmangafodipir, significantly more efficacious than 1 and 10 mg/kg mangafodipir protecting WBC. Similar falls were seen in lymphocytes (LYM; FIG. 8B) and in neutrophils (NEU; FIG. 8C) after oxaliplatin treatment. Qualitatively similar results were also obtained when neutrophils (NEU) were analyzed (FIG. 8C). Regarding platelets (PLC; FIGS. 7D and 8D, in comparison to WBC, LYM and NEU they differed both in the sensitivity towards oxaliplatin and the cytoprotective effects of the test substances.

Conclusion

Calmangafodipir was at an equimolar manganese dose significantly more potent than mangafodipir to protect balb/c mice against myelosuppressive effects of the anticancer drug oxaliplatin.

Example 6

The cytotoxic activity in murine colon cancer cells of calmangafodipir was compared with that of mangafodipir, fodipir, MnPLED, ZnPLED, ZnDPDP, calfodipir (CaDPDP), PLED, and $CaCl_2$.

Method

The viability of cells was measured using the MTT assay. Briefly, 8,000 CT26 (mouse colon carcinoma) cells were seeded per well on a 96-well plate and grown over night in RPMI (Roswell Park Memorial Institute) 1640 medium containing 10% fetal bovine serum, 2 mM L-glutamine, 100 UI/ml penicillin and 100 µg/ml streptomycin at 37° C. in humidified air with 5% $CO_2$. Cells were then exposed for 48 h to 1-1,000 µM calmangafodipir (lot #11AK0105B), fodipir (DPDP; lot #RDL02090206), PLED (lot #KER-AO-122(2)), calfodipir (CaDPDP), mangafodipir (lot #02090106), MnPLED, ZnPLED, ZnDPMP and $CaCl_2$ at 37° C. The viability of the cells was then assessed by adding 5 mg/ml methylthiazoletetrazolium (MTT) to a final concentration of 0.5 mg/ml and incubating cells for a further 4 h at 37° C. The blue formazan that is formed by mitochondrial dehydrogenases of viable cells was then dissolved over night at 37° C. by adding 10% SDS and 10 mM HCl to a final concentration of 5% SDS and 5 mM HCl. Finally, the absorbance of the solution was read at 570 nm with a reference at 670 nm in a microplate reader Spectramax 340 (Molecular Devices, Sunnyvale, Calif., USA) connected to an Apple Macintosh computer running the program Softmax Pro V1.2.0 (Molecular Devices, Sunnyvale, Calif., USA).

Results

Figure 9A:
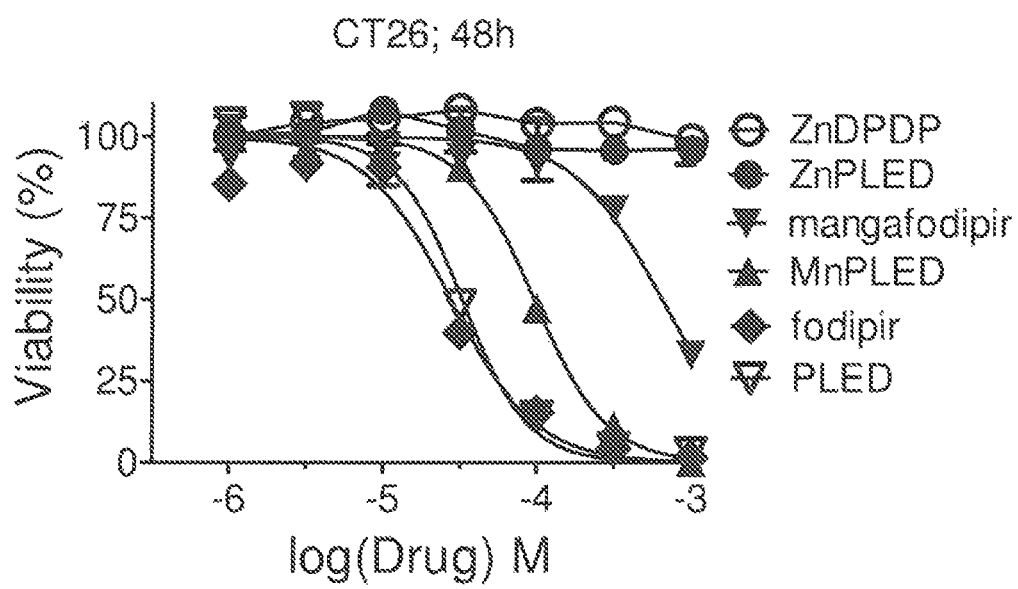
FIGS. 9A-9B show the cytotoxic activity of various PLED-derivatives and CaCl$_2$ at increasing concentrations on colon cancer CT26 cells. The results are expressed as mean±S.D.; n=3), as described in Example 6.
Figure 9B:
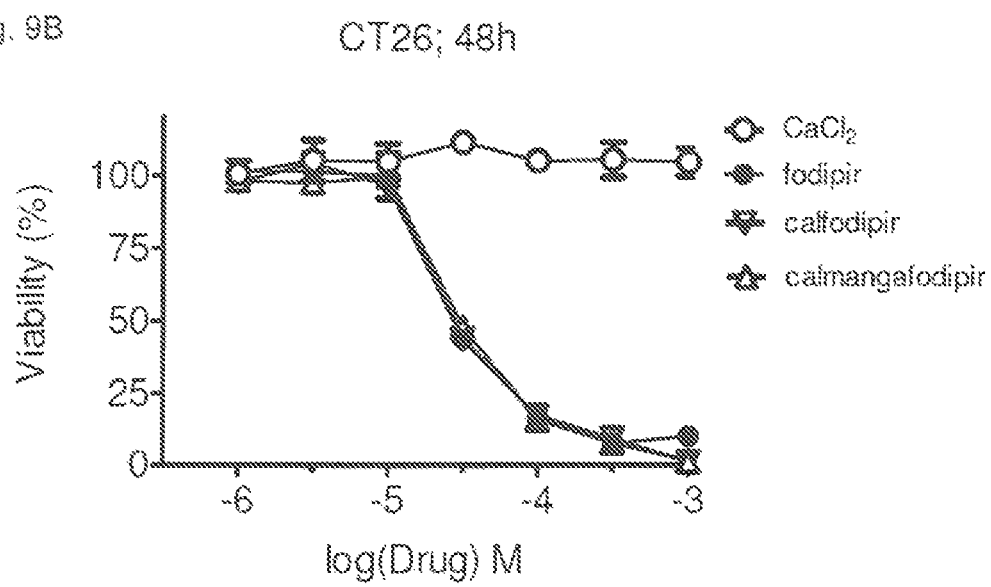

The cytotoxic activity of fodipir, PLED, calfodipir or calmangafodipir was about 20 times higher than that of mangafodipir (FIGS. 9A and 9B). MnPLED was almost 10 times more potent than mangafodipir in its ability to kill CT26 cancer cells (FIG. 9A). Neither ZnDPDP, ZnPLED nor $CaCl_2$ displayed any cytotoxic activity at all at the used concentrations (FIGS. 9A and 9B).

Conclusion

When calmangafodipir and mangafodipir were compared, calmangafodipir was found to be about 20 times more potent than mangafodipir to kill CT26 cancer cells. Dissociation of manganese to some extent from fodipir probably explains the cancer killing efficacy of mangafodipir. Calmangafodipir as defined in Examples 1 and 3, at manganese equimolar concentrations, is on the other hand as efficacious as fodipir alone, i.e., the killing efficacy of calmangafodipir is much higher than that of mangafodipir at equimolar manganese concentrations. This finding suggests two important properties. Firstly, dephosphorylated PLED is probably as efficacious as its phosphorylated counterpart fodipir with respect to its cancer cell killing ability, and secondly, the lower stability of MnPLED in comparison to that of mangafodipir (Rocklage et al., 1989) probably explains the higher efficacy of MnPLED. The lack of any cytotoxic activity of ZnDPDP and ZnPLED is presumably due to the 1000 times higher stability of these complexes in comparison to their manganese counterparts (Rocklage et al., 1989).

Example 7

This example compares the antitumor activity of oxaliplatin in a murine colon cancer (CT26)-bearing mice model in the presence and absence of calmangafodipir.

Method

CT26 cells were grown in 75 $cm^2$ culture flasks in RPMI (Roswell Park Memorial Institute) 1640 medium containing 10% fetal bovine serum, 2 mM L-glutamine, 100 UI/ml penicillin and 100 µg/ml streptomycin at 37° C. in humidified air with 5% $CO_2$. When the cells reached ~50% confluency they were harvested by trypsinization. Briefly, cells were washed with phosphate based saline (PBS) (pH 7.3) and exposed to 0.05% Trypsin/0.53 mM EDTA at 37° C. for ~5 mM The trypsinization was stopped by adding RPMI1640 culture medium. Cells were counted and centrifuged at 200×g for 5 min. Thereafter, they were washed in PBS, centrifuged again and resuspended in PBS at a concentration of $2\times10^6/350$ µl for injection into mice. Balb/c female mice between 6 and 8 weeks of age were used, as described by Laurent et al., 2005. Briefly, each mouse was injected subcutaneously in the back of the neck with $2\times10^6$ of CT26 cells at day 0. After 7 days (day 7) when the tumors were detectable, the tumor size was determined with a caliper and mice were grouped (5 in each group) so that the sizes of the tumors were not statistically different by group. Oxaliplatin±calmangafodipir (lot #11AK0105B) was injected and one group of mice received vehicle (0.9% saline+5% glucose) treatment alone. In a first series of experiments, mice were injected i.v. with saline or 50 mg/kg calmangafodipir 30 minutes prior to i.p. administration of 20 mg/kg oxaliplatin (diluted in 5% glucose) or 5% glucose. These mice received in addition saline or 50 mg/kg calmangafodipir 24 hours later (day 8). In another series of experiments, mice were injected i.v. with saline or 5 mg/kg calmangafodipir 30 minutes 10 mg/kg oxaliplatin (diluted in 5% glucose) or 5% glucose, and saline or 5 mg/kg calmangafodipir 24 hours later (day 8). The mice were killed on day 10 and the tumors were excised and wet weights were determined. The statistical differences between treatment groups, where appropriate, were tested by an unpaired Student's t-test. A p-value lower than 0.05 was considered as a statistically significant difference.

Results

Figure 10A:
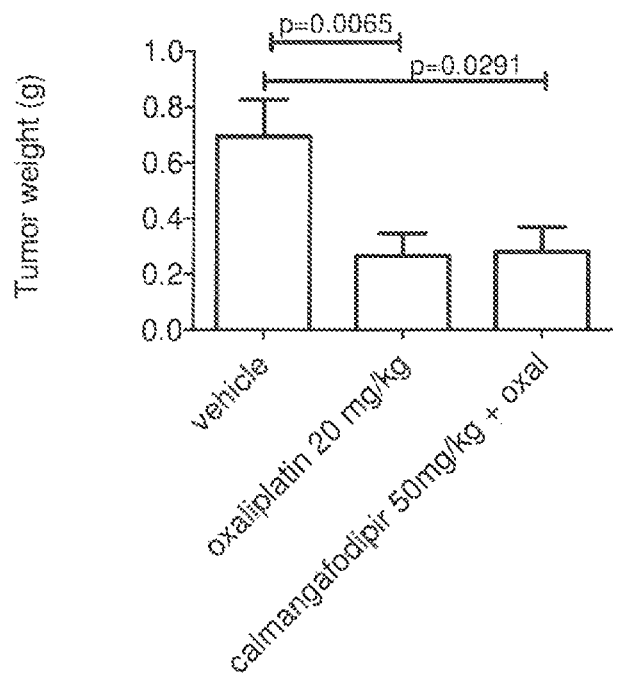
FIG. 10A shows the antitumor effect of a high dose oxaliplatin (20 mg/kg) in CT26 syngenic balb/c mice in the absence and presence of a relatively high dose of calmangafodipir (50 mg/kg).
Figure 10B:
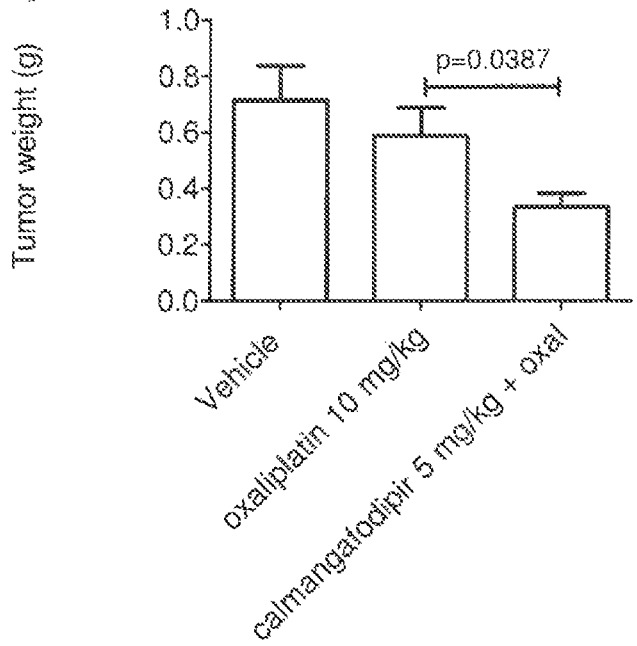
FIG. 10B shows the antitumor effect of a low dose of oxaliplatin (10 mg/kg in the absence and presence of a relatively low dose of calmangafodipir. Results are expressed as mean±S.E.M.; n=10 in vehicle and oxaliplatin 20 mg/kg groups in FIG. 10A; n=5 in all other groups), as described in Example 7.

The results are set forth in FIGS. 10A and 10B. In the first series of experiment the mice received 20 mg/kg oxaliplatin, which is close to the highest tolerated dose. Single treatment with oxaliplatin resulted in a statistically significant and more than 50% reduction in tumor weight. Treatment with calmangafodipir (50 mg/kg) did not have any negative influence on the antitumor effect of oxaliplatin at a high dose (FIG. 10A). However, in a second series of experiments in which 10 mg/kg oxaliplatin was used, treatment with a relatively low dose of calmangafodipir (5 mg/kg) resulted in a statistically significant better antitumor effect (FIG. 10B); the combined effect of 10 mg/kg oxaliplatin plus 5 mg/kg calmangafodipir was almost as efficacious as 20 mg/kg oxaliplatin alone.

Conclusion

Calmangafodipir did not interfere negatively with the antitumor activity of oxaliplatin, and, to the contrary, at a relatively low dose of oxaliplatin (10 mg(kg), calmangafodipir actually increased the antitumor efficacy.

Example 8

This example compares levels of manganese after repeated intravenous injections of calmangafodipir and mangafodipir (39 times over 33 weeks) in the rat brain, pancreas and liver.

Method

Wistar male and female rats were intravenously injected with either 0.9% NaCl, 72.0 µmol/kg mangafodipir (lot #02090106; corresponding to 72 µmol/kg of manganese) or 374.4 µmol/kg calmangafodipir (lot #11AK0105B; corresponding to 72 µmol/kg of manganese) 3 times a week for 13 weeks (each treatment group consisted of 9 males+9 females). Each dose of calmangafodipir corresponded to about 36 times the assumed clinical dose (ACD). After the 13-week administration period, the rats were sacrificed and the brains and pancreas were dissected out and approximately 0.5 g samples were stored frozen until Mn analysis. The Mn content of each sample was analyzed by ICP-MS. Results are expressed as µg/g wet weight±S.E.M. Statistical difference between the mangafodipir group and the calmangafodipir group, with respect to Mn content, was tested by a paired Student's t-test. A p-value lower than 0.05 was considered as a statistically significant difference.

Results

Figure 11A:
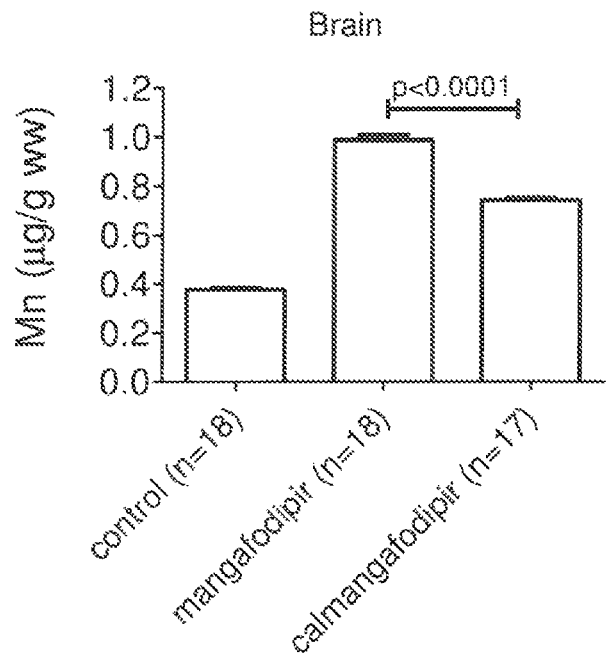
Figure 11B:
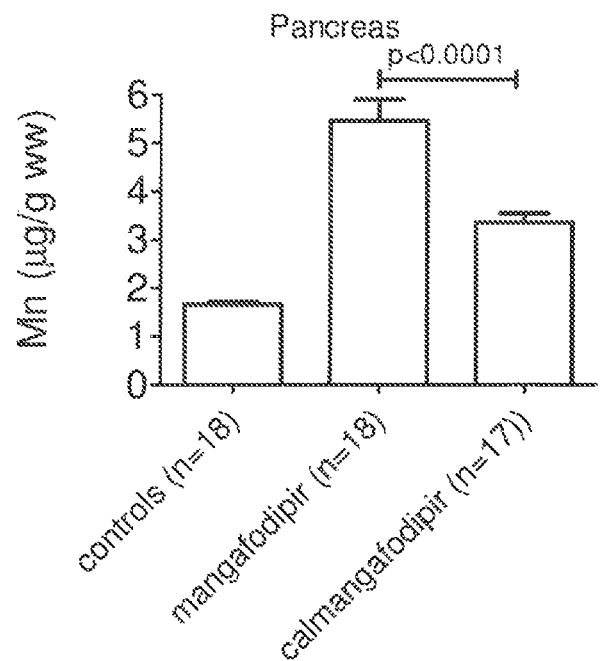
Figure 12A:
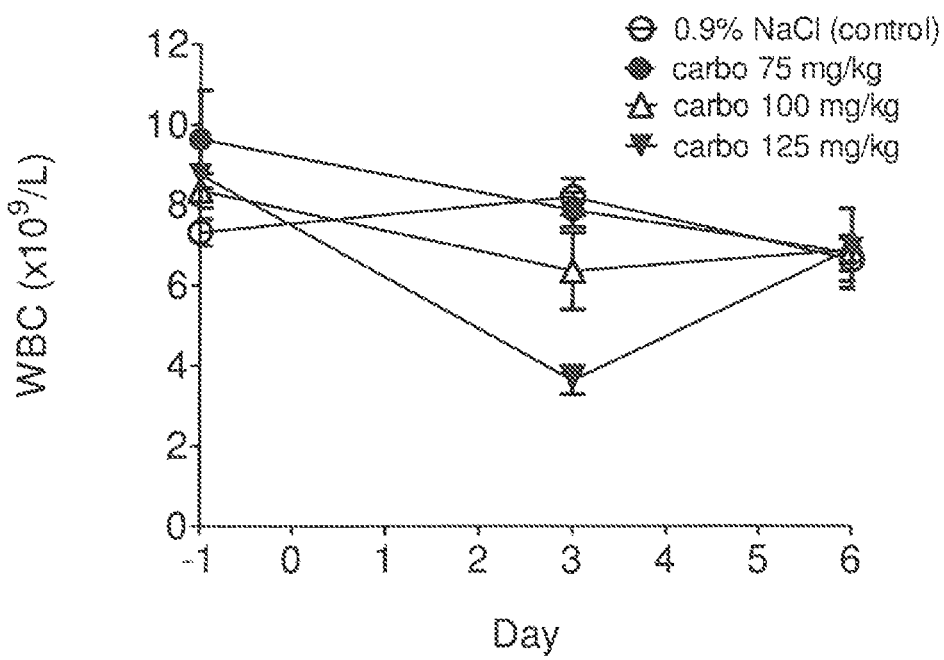
FIGS. 12A-12D show the myelosuppressive effects on white blood cells (WBC), lymphocytes (LYM), neutrophils (NEU), and platelets (PLC), respectively, of single intravenous injection of increasing doses (75, 100 and 125 mg/kg) of carboplatin at 3 and 6 days post injection. Results expressed as mean±S.E.M.; n=5 in each group, as described in Example 9.
Figure 12B:
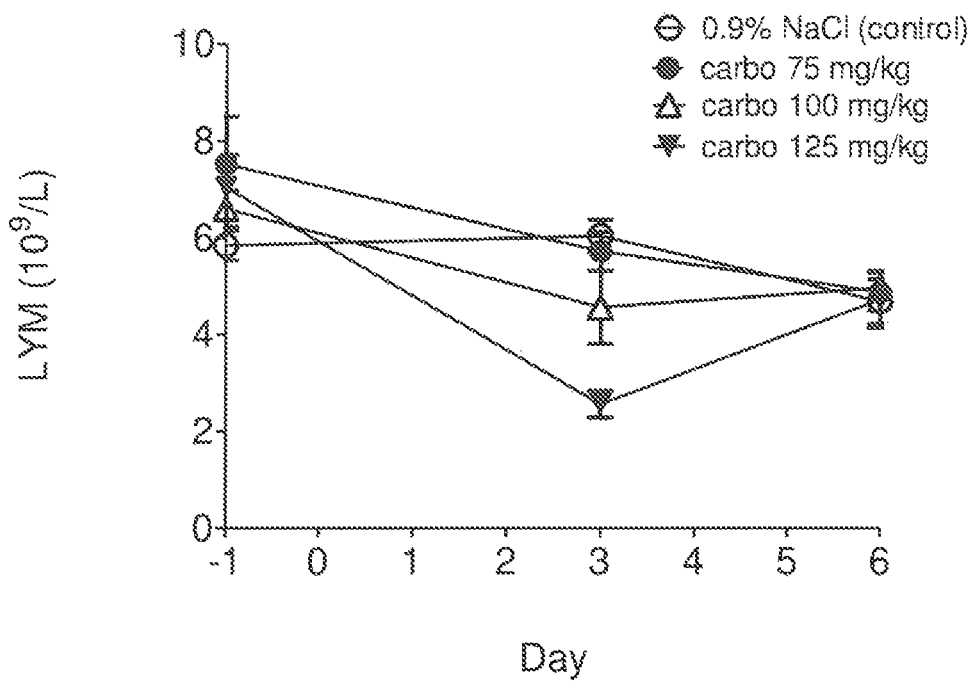
Figure 12:
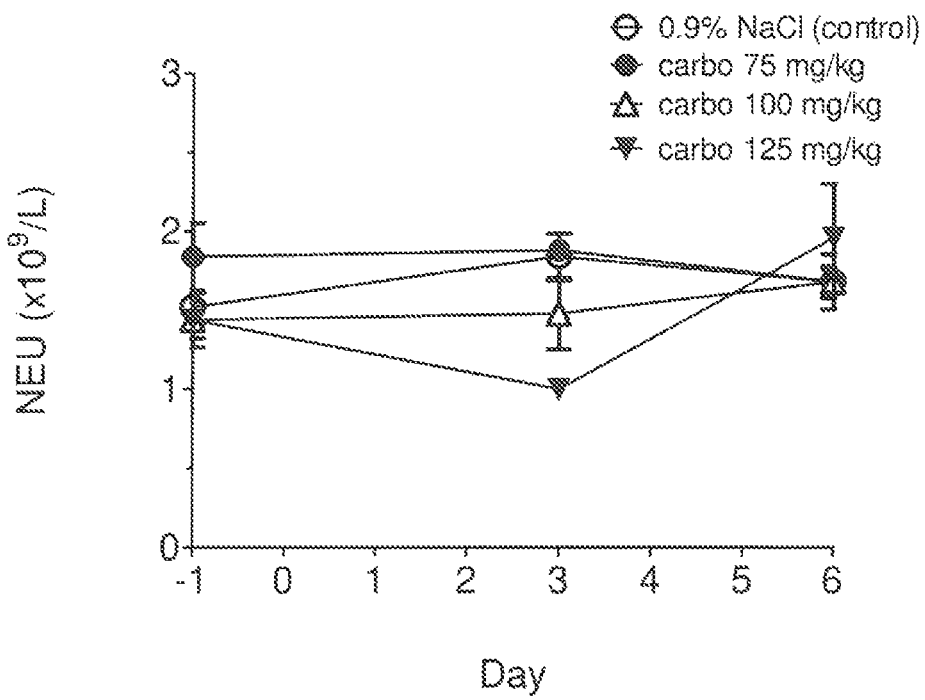
Figure 12D:
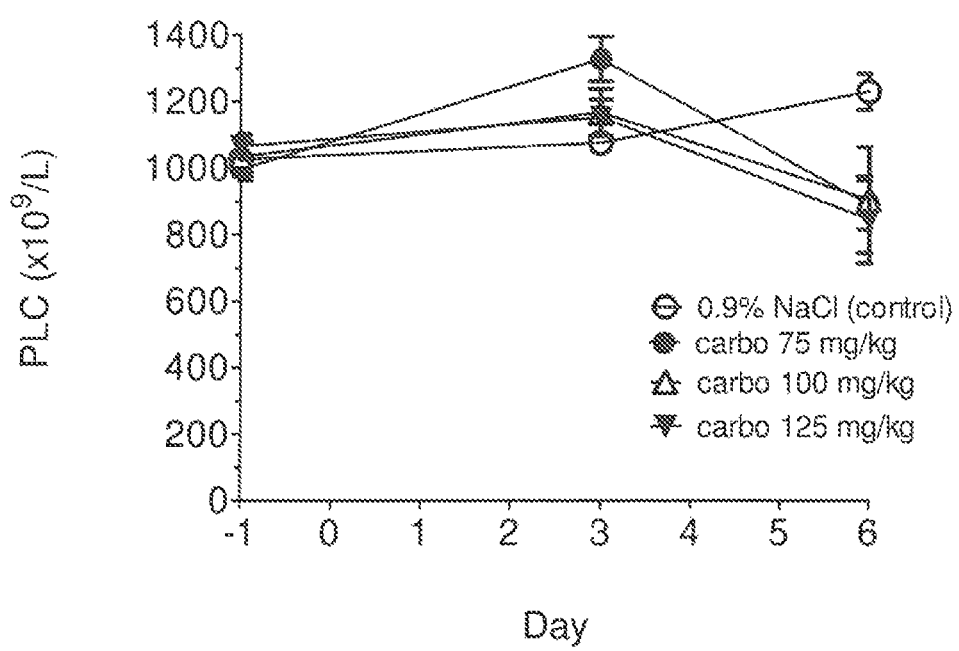
Figure 13:
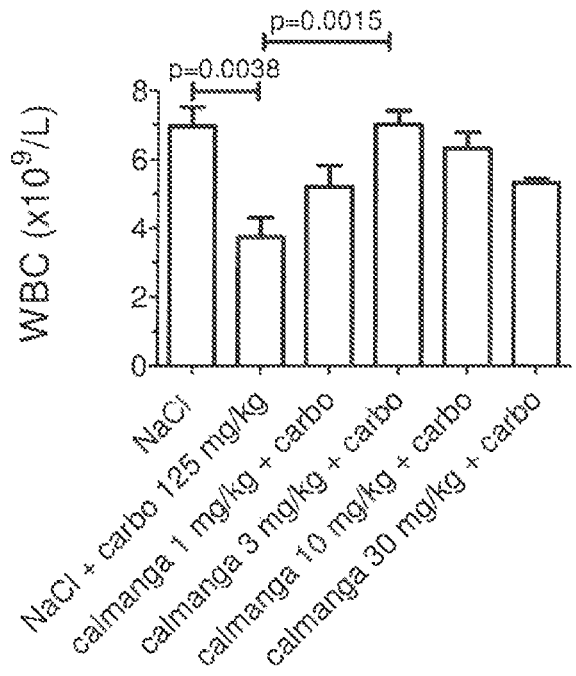
FIGS. 13A-13D show WBC, LYM, NEU and PLC, respectively after carboplatin in combination with calmangafodipir in balb/c mice. Controls received vehicle treatment only. Results expressed as mean±S.E.M.; n=5 in each group, as described in Example 9.
Figure 13B:
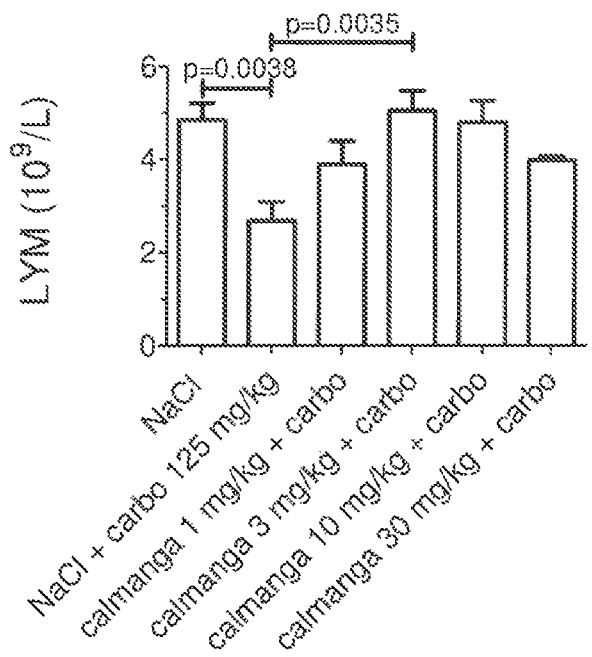
Figure 13C:
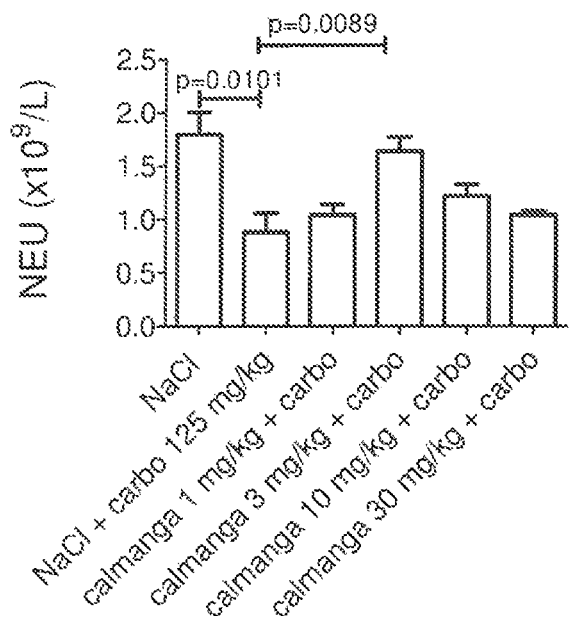
Figure 13D:
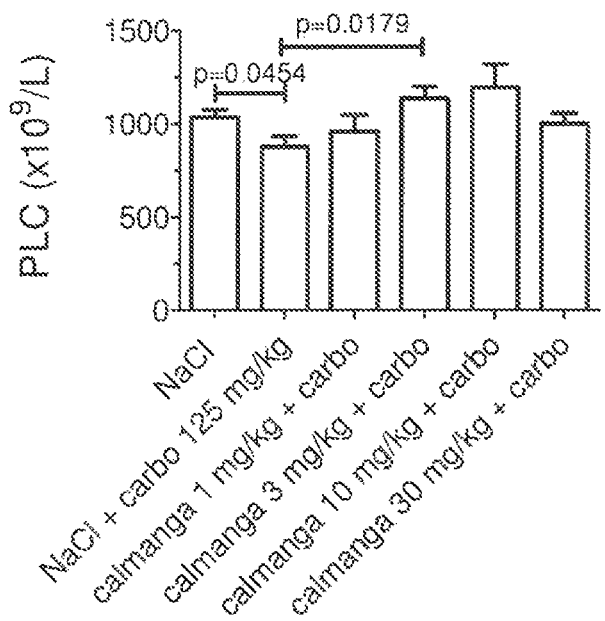

Results are set forth in FIGS. 11A-C. The Mn brain content in NaCl-treated control rats, mangafodipir-treated rats, and calmangafodipir-treated rats was 0.38±0.01, 0.99±0.02 and 0.74±0.01 µg/g w.w., respectively. The corresponding Mn content in the pancreas was 1.66±0.06, 5.54±0.45 and 3.35±0.19 µmol/kg, respectively. Although, the Mn content of the liver was statistically significant elevated in the mangafodipir group (FIG. 11C), the relative elevation was much less than those seen in the brain and pancreas.

Conclusion

Administration of a high accumulated dose of calmangafodipir into rats results in significantly less retention of manganese in the brain and pancreas compared to mangafodipir (the total dose in both cases corresponded to approximately 2800 µmol/kg of manganese). These results demonstrate the improved toxicological profile of calmangafodipir in comparison to that of mangafodipir.

Example 9

This example shows the cytoprotective effect of calmangafodipir with respect to myelosuppressive effects of carboplatin in balb/c mice.

Method

In a first series of experiments, 3 groups, each consisting of 5 female balb/c mice, were treated once intraperitoneally with carboplatin at 75, 100 and 125 mg/kg carboplatin, respectively. One day before (baseline), as well as 3 and 6 days after, carboplatin treatment, 50 µl EDTA blood samples were taken from the orbital venous plexus with a glass capillary. The blood samples were analyzed using the automated system CELL-DYN® Emerald (Abbott Diagnostics) for the content of white blood cells (WBC), lymphocytes (LYM), neutrophils (NEU) and platelets (PLC). From the results (FIGS. 12A-12D), it was concluded that further experiments testing the myeloprotective effect of calmangafodipir should be performed at 125 mg/kg carboplatin and that, in case of WBC, NEU and LYM, blood cell sample analyses should be performed the day before and 3 days after carboplatin administration, and, in case of PLC, blood cell sample analysis should be performed the day before and 6 days after carboplatin administration. Thirty minutes before administration of carboplatin (125 mg/kg) and 24 hours after, the mice received saline or calmangafodipir (1, 3, 10 or 30 mg/kg; lot #11AK0105B). A control group received vehicle (saline) and saline instead of carboplatin. The results are presented in graphs as relative changes from baseline for the various treatments (mean±S.E.M.). The statistical differences between treatment groups, where appropriate, were tested by an unpaired Student's t-test. A p-value lower than 0.05 was considered as a statistically significant difference.

Results

The results are set forth in FIGS. 13A-13D. Carboplatin (125 mg/kg) caused an approximately 50% decrease in WBC, as well as in NEU and LYM. Treatment with calmangafodipir at a dose of 3 mg/kg abolished these decreases. The dose-response of calmangafodipir displayed a bell shaped appearance in each case, in a similar way as previously described for mangafodipir with respect to its cardioprotective effect against doxorubicin in CD mice (Kurz et al., Transl Oncol 2012; 5:252-259).

Regarding platelets (PLC, FIGS. 12D and 13D), in comparison to WBC, LYM and NEU, they differed in the sensitivity towards carboplatin.

Conclusion

Calmangafodpir profoundly protects balb/c mice against myelosuppressive effects of the anticancer drug carboplatin.

Example 10

This example compares the antitumor activity of oxaliplatin in colon cancer (CT26)-bearing immune competent balb/c mice and immune deficient nude balb/c mice (nu/nu) in the presence and absence of calmangafodipir.

Method

Figure 14:
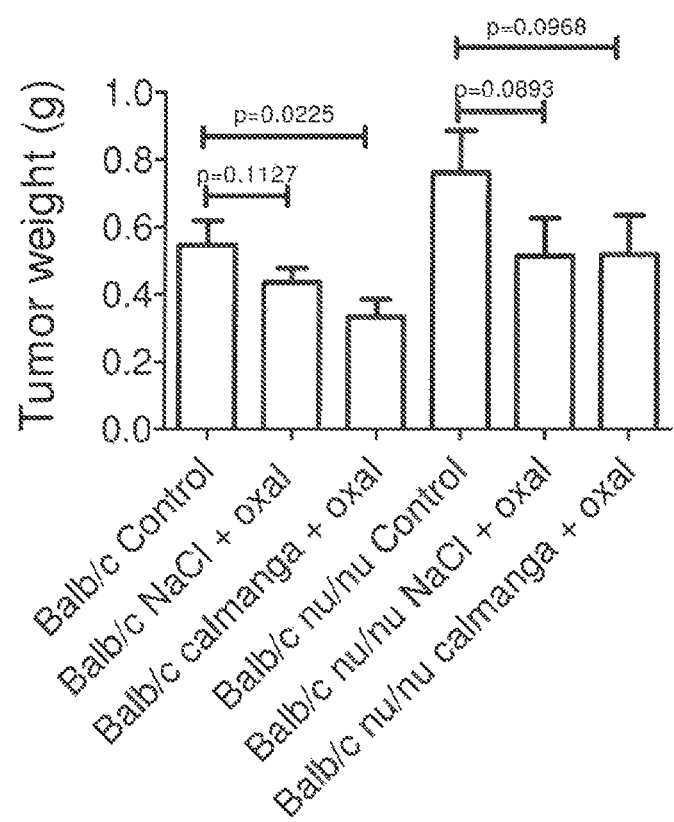
FIG. 14 shows the antitumor effect of a low dose of oxaliplatin (10 mg/kg) in CT26 bearing immune competent balb/c mice and in immune deficient nude balb/c mice (nu/nu) in the absence and presence of a relatively low dose of calmangafodipir. Results are expressed as ±S.E.M.; n=5 in each group, as described in Example 10.

CT26 cells were grown in 75 $cm^2$ culture flasks in RPMI 1640 medium containing 10% fetal bovine serum, 2 mM L-glutamine, 100 UI/ml penicillin and 100 µg/ml streptomycin at 37° C. in humidified air with 5% $CO_2$. When the cells reached ~50% confluency they were harvested by trypsinization. Briefly, cells were washed with PBS (pH 7.3) and exposed to 0.05% Trypsin/0.53 mM EDTA at 37° C. for ~5 mM The trypsinization was stopped by adding RPMI 1640 culture medium. Cells were counted and centrifuged at 200×g for 5 min. Thereafter, they were washed in PBS, centrifuged again and resuspended in PBS at a concentration of $2\times10^6$/ 350 µl for injection into mice Immune competent balb/c female mice (balb/c) and immune incompetent nude female balb/c mice (blab/c nu/nu) between 6 and 8 weeks of age were used, as described by Laurent et al., 2005. Briefly, each mouse was injected subcutaneously in the back of the neck with $2\times10^6$ of CT26 cells at day 0. After 7 days (day 7) when the tumors were detectable, the tumor size was determined with a caliper and mice were grouped (5 in each group) so that the sizes of the tumors were not statistically different by group. Groups of mice (5 in each group, as illustrated in FIG. 14) were injected i.v. with saline or 5 mg/kg calmangafodipir (lot #11AK0105B) 30 minutes prior to i.p. administration of 10 mg/kg oxaliplatin (diluted in 5% glucose) or 5% glucose. Mice received in addition saline or 5 mg/kg calmangafodipir 24 hours later (day 8). The mice were sacrificed on day 10 and the tumors were excised and wet weights were determined. The results are presented in a graph for the various treatments (mean±S.E.M.). The statistical differences between treatment groups, where appropriate, were tested by an unpaired Student's t-test. A p-value lower than 0.05 was considered as a statistically significant difference.

Results

The results are set forth in FIG. 14. There was clear tendency that the tumors grew larger in the immune deficient balb/c mice than in immune competent balb/c nu/nu mice but this difference did not reach statistical significance (p=0.0870). A single treatment with 10 mg/kg oxaliplatin resulted in statistically insignificant 20 to 30% reduction in tumor weights in immune competent and immune deficient balb/c mice. Treatment with 5 mg/kg calmangafodipir did not have any negative influence on the antitumor effect of oxaliplatin in either the immune competent or in the immune incompetent mice. The mean tumor weight was actually statistically significantly reduced in the immune competent mice treated with 5 mg/kg calmangafodipir compared to controls. However, no such reduction was seen in the immune deficient mice.

Conclusion

Calmangafodipir did not interfere negatively with the antitumor activity of oxaliplatin in either immune competent or immune deficient mice but it was only in immune competent mice that calmangafodipir actually increased the antitumor efficacy.

Example 11

The cytotoxic activity of calmangafodipir toward human non-small cell lung cancer (NSCLC) U1810 cells and murine non-small cell lung cancer (LLC1) was compared with that of mangafodipir.

Methods

The viability of cells was measured using the MTT assay. Briefly, 8,000 human U1810 NSCLC or LLC1 NSCLC cells were seeded per well on a 96-well plate and grown over night in RPMI (Roswell Park Memorial Institute) 1640 medium containing 10% fetal bovine serum, 2 mM L-glutamine, 100 UI/ml penicillin and 100 µg/ml streptomycin at 37° C. in humidified air with 5% $CO_2$. Cells were then exposed for 48 h to 1-1,000 µM calmangafodipir (lot #11AK0105B) or mangafodipir (lot #02090106). The viability of the cells was then assessed by adding 5 mg/ml methylthiazoletetrazolium (MTT) to a final concentration of 0.5 mg/ml and incubating cells for a further 4 h at 37° C. The blue formazan that is formed by mitochondrial dehydrogenases of viable cells was then dissolved over night at 37° C. by adding 10% SDS and 10 mM HCl to a final concentration of 5% SDS and 5 mM HCl. Finally, the absorbance of the solution was read at 570 nm with a reference at 670 nm in a microplate reader Spectramax 340 (Molecular Devices, Sunnyvale, Calif., USA) connected to an Apple Macintosh computer running the program Softmax Pro V1.2.0 (Molecular Devices, Sunnyvale, Calif., USA). The viability of U1810 or LLC1 cells in the presence of increasing concentrations of calmangafodipir or mangafodipir is presented as concentration response curves (mean±S.D.). The individual curves were fitted to the sigmoidal variable slope response logistic equation (Graphpad Prism, version 5.02). From this analysis the concentrations causing 50% inhibition ($IC_{50}$) of the test substances were calculated.

Results

Figure 15A:
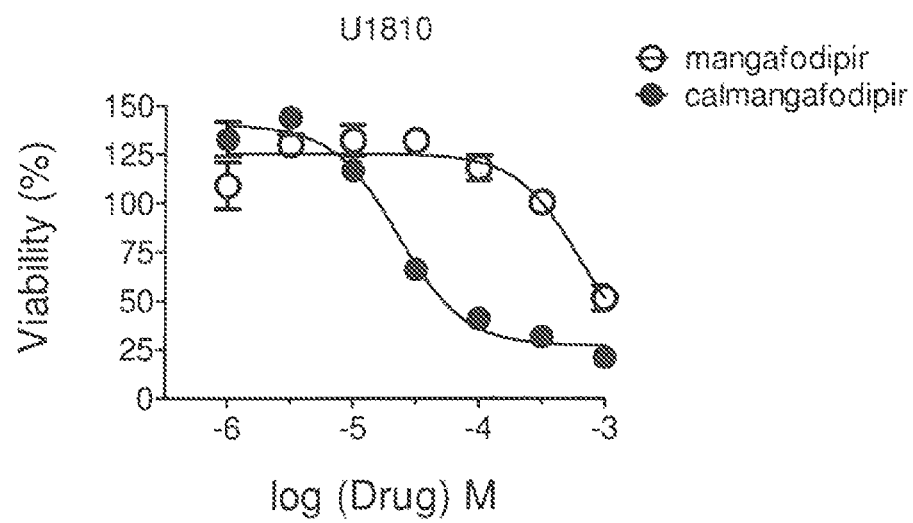
FIGS. 15A and 15B show the cytotoxic activity of calmangafodipir and mangafodipir in non-small cell lung cancer cells U1810 and LLC1, respectively. The results are expressed as mean±S.D.; n=3, as described in Example 11.
Figure 15B:
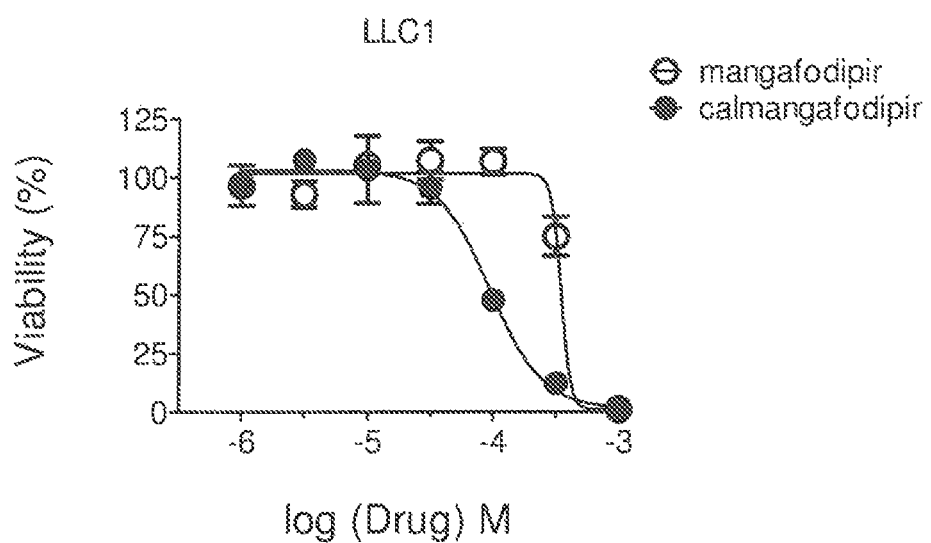

The cytotoxic activity of calmangafodipir and mangafodipir toward NSCLC U1810 and LLC1 cells is shown in FIGS. 15A and 15B. The calculated $IC_{50}$ ratio between mangafodipir and calmangafodipir (0.0006329/0.00002274) showed that calmangafodipir was about 28 times more potent than mangafodipir to kill U1810 cells (FIG. 15A). Although calmangafodipir was significantly more potent than mangafodipir to kill LLC1 cells, because of the ambiguous appearance of the mangafodipir curve (FIG. 15B) it was not meaningful to calculate an $IC_{50}$ ratio between mangafodipir and calmangafodipir.

Conclusions

The results demonstrate the superior efficacy of calmangafodipir in comparison to mangafodipir to kill the non-small cell lung cancer cells, U1810 and LLC1.

The examples and specific embodiments set forth herein are illustrative in nature only and are not to be taken as limiting the scope of the invention defined by the following claims Additional specific embodiments and advantages of the present invention will be apparent from the present disclosure and are within the scope of the claimed invention.

What is claimed is:

1. A mixed metal complex of a compound of Formula I, or a salt thereof, wherein the mixed metals comprise calcium and manganese and wherein the molar ratio of calcium to manganese is 1-10:

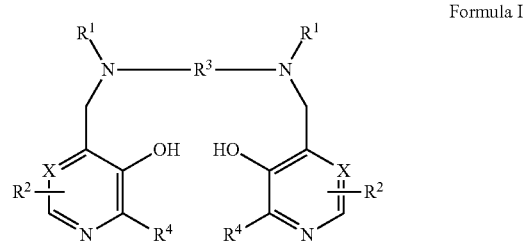

Formula I wherein

X represents CH or N, each $R^1$ independently represents hydrogen or —$CH_2COR^5$;

$R^5$ represents hydroxy, ethylene glycol, glycerol, optionally hydroxylated alkoxy, amino or alkylamido;

each $R^2$ independently represents $ZYR^6$ wherein Z represents a bond, CO, or a $C_{1-3}$ alkylene or oxoalkylene group, optionally substituted by $R^7$;

Y represents a bond, an oxygen atom or $NR^6$;

$R^6$ is a hydrogen atom, $COOR^8$, alkyl, alkenyl, cycloalkyl, aryl or aralkyl group, optionally substituted by one or more groups selected from $COOR^8$, $CONR^8_2$, $NR^8_2$, $OR^8$, $=NR^8$, $=O$, $OP(O)(OR^8)R^7$ and $OSO_3M$;

$R^7$ is hydroxy, optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation;

$R^3$ represents a $C_{1-8}$ alkylene, a 1,2-cykloalkylene, or a 1,2-arylene group, optionally substituted with $R^7$; and each $R^4$ independently represents hydrogen or $C_{1-3}$ alkyl.

2. A mixed metal complex according to claim 1, wherein $R^5$ is hydroxy, $C_{1-8}$ alkoxy, ethylene glycol, glycerol, amino or $C_{1-8}$ alkylamido; Z is a bond or a group selected from $CH_2$, $(CH_2)_2$, CO, $CH_2CO$, $CH_2CH_2CO$ and $CH_2COCH_2$; Y is a bond; $R^6$ is a mono- or poly(hydroxy or alkoxylated) alkyl group or of the formula $OP(O)(OR^8)R^7$; and $R^7$ is hydroxy, or an unsubstituted alkyl or aminoalkyl group.

3. A mixed metal complex according to claim 1, wherein $R^3$ is ethylene and each group $R^1$ represents —$CH_2COR^5$ in which $R^5$ is hydroxy.

4. A mixed metal complex according to claim 1, wherein the compound of Formula I is N,N'-bis-(pyridoxal-5-phosphate)-ethylenediamine-N,N'-diacetic acid (DPDP) or N,N'- dipyridoxyl ethylenediamine-N,N'-diacetic acid (PLED), or a pharmaceutically acceptable salt thereof.

5. A mixed metal complex according to claim 1, having a $Ca^{2+}/Mn^{2+}$ molar ratio of about 4.

6. A mixed metal complex according to claim 1, wherein the mixed metal complex is a mixed metal complex of a sodium salt of a compound of Formula I.

7. A mixed metal complex according to claim 2, having a $Ca^{2+}/Mn^{2+}$ molar ratio of about 4.

8. A mixed metal complex according to claim 3, having a $Ca^{2+}/Mn^{2+}$ molar ratio of about 4.

9. A mixed metal complex according to claim 4, having a $Ca^{2+}/Mn^{2+}$ molar ratio of about 4.

10. A mixed metal complex according to claim 1, wherein the complex is freeze dried.

11. A pharmaceutical composition comprising a mixed metal complex according to claim 1 and one or more physiologically acceptable carriers and/or excipients.

12. A method of producing a mixed metal complex according to claim 1, comprising a one-step crystallization from a solution of calcium, manganese, and a compound of Formula I, or a salt thereof.

13. A method for treatment of a cytotoxic or cytostatic drug injury in a patient, comprising administering to the patient an effective amount of a mixed metal complex according to claim 1.

14. A method according to claim 13, wherein the cytotoxic or cytostatic drug is a cancer treatment drug.

15. A method according to claim 13, wherein the cytotoxic or cytostatic drug comprises at least one of doxorubicin, epirubicin, oxaliplatin, carboplatin, cisplatin, 5-fluorouracil, docetaxel or paclitaxel.

16. A method according to claim 13, wherein the cytotoxic or cytostatic drug injury is myelosuppression.

17. A method for treatment of acetaminophen-induced acute liver failure in a patient, comprising administering to the patient an effective amount of a mixed metal complex according to claim 1.

18. A method for treatment of non-small cell lung cancer or colorectal cancer in a patient, comprising administering to the patient an effective amount of a mixed metal complex according to claim 1.

19. A method according to claim 13, comprising administering about 0.01 to 50 µmol/kg body weight of the mixed metal complex.

20. A method according to claim 13, comprising administering about 0.1 to 10 µmol/kg body weight of the mixed metal complex.

21. A method according to claim 20, having a $Ca^{2+}/Mn^{2+}$ molar ratio of about 4.

22. A method according to claim 21, wherein the mixed metal complex is a mixed metal complex of a sodium salt of a compound of Formula I.

23. A method according to claim 13, comprising administering about 0.1 to 5 µmol/kg µmol/kg body weight of the mixed metal complex.

24. A method according to claim 18, comprising administering about 0.01 to 50 µmol/kg body weight of the mixed metal complex.

25. A method according to claim 18, comprising administering about 0.1 to 10 µmol/kg body weight of the mixed metal complex.

26. A method according to claim 25, having a $Ca^{2+}/Mn^{2+}$ molar ratio of about 4.

27. A method according to claim 26, wherein the mixed metal complex is a mixed metal complex of a sodium salt of a compound of Formula I.

28. A method according to claim 18, comprising administering about 0.1 to 5 µmol/kg µmol/kg body weight of the mixed metal complex.

29. A method according to claim 13, wherein the cytotoxic or cytostatic drug injury is neurotoxicity.

30. A method according to claim 29, wherein the cytotoxic or cytostatic drug comprises oxaliplatin.

31. A method according to claim 29, comprising administering about 0.01 to 50 µmol/kg body weight of the mixed metal complex.

32. A method according to claim 29, comprising administering about 0.1 to 10 µmol/kg body weight of the mixed metal complex.

33. A method according to claim 32, having a $Ca^{2+}/Mn^{2+}$ molar ratio of about 4.

34. A method according to claim 33, wherein the mixed metal complex is a mixed metal complex of a sodium salt of a compound of Formula I.

35. A method according to claim 29, comprising administering about 0.1 to 5 µmol/kg µmol/kg body weight of the mixed metal complex.

36. A method according to claim 17, comprising administering about 0.01 to 50 µmol/kg body weight of the mixed metal complex.

37. A method according to claim 17, comprising administering about 0.1 to 10 µmol/kg body weight of the mixed metal complex.

38. A method according to claim 37, having a $Ca^{2+}/Mn^{2+}$ molar ratio of about 4.

39. A method according to claim 38, wherein the mixed metal complex is a mixed metal complex of a sodium salt of a compound of Formula I.

40. A method according to claim 17, comprising administering about 0.1 to 5 µmol/kg µmol/kg body weight of the mixed metal complex.

41. A mixed metal complex according to claim 1, wherein
X represents CH,
each $R^1$ represents —$CH_2COR^5$;
$R^5$ represents hydroxy;
each $R^2$ independently represents $ZYR^6$ wherein Z represents a bond, —$CH_2$— or —$CH_2O$—;
Y represents a bond or an oxygen atom;
$R^6$ is a hydrogen atom, $COOR^8$, $C_1$-$C_8$ alkyl, or $C_1$-$C_8$ alkenyl group optionally substituted by one or more groups selected from $COOR^8$, $CONR^8_2$, $NR^8_2$, $OR^8$, =$NR^8$, =O, $OP(O)(OR^8)R^7$ and $OSO_3M$;
$R^7$ is hydroxy, optionally hydroxylated, optionally $C_1$-$C_8$ alkoxylated $C_1$-$C_8$ alkyl or amino-$C_1$-$C_8$-alkyl group; and
$R^8$ is a hydrogen atom or an optionally hydroxylated, optionally $C_1$-$C_8$ alkoxylated $C_1$-$C_8$ alkyl group;
provided that each $ZYR^6$ includes a —$CH_2O$— linkage to the respective pyridine ring;
M is a hydrogen atom or one equivalent of a physiologically tolerable cation;
$R^3$ represents ethylene; and
each $R^4$ independently represents hydrogen or $C_{1-3}$ alkyl.

\* \* \* \* \*